(12) United States Patent
Chen

(10) Patent No.: US 6,218,397 B1
(45) Date of Patent: Apr. 17, 2001

(54) PYRAZOLOPYRIMIDINES AS CRF ANTAGONISTS

(75) Inventor: Yuhpyng Liang Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/148,075

(22) Filed: Sep. 4, 1998

Related U.S. Application Data

(63) Continuation of application No. 08/481,413, filed as application No. PCT/US93/11333 on Nov. 26, 1993, now abandoned, which is a continuation-in-part of application No. 07/992,229, filed on Dec. 17, 1992, now abandoned.

(51) Int. Cl.⁷ .................. C07D 487/04; A61K 31/519
(52) U.S. Cl. ........................ 514/258; 544/262
(58) Field of Search ................. 544/262; 514/258

(56) References Cited

U.S. PATENT DOCUMENTS

| | | | |
|---|---|---|---|
| 2,965,643 | 12/1960 | Druey et al. | 544/118 |
| 3,036,070 | 5/1962 | Druey et al. | 544/118 |
| 3,551,428 | 12/1970 | Druey et al. | 544/262 |
| 3,600,389 | 8/1971 | Druey et al. | 544/118 |
| 4,139,705 | 2/1979 | Dunbar et al. | 544/116 |
| 4,426,384 | 1/1984 | Wyburn-Maso | 514/258 |
| 4,605,642 | 8/1986 | Rivier | 514/12 |
| 4,904,666 | 2/1990 | Friebe | 544/262 |
| 5,063,245 | 11/1991 | Abreu et al. | 514/404 |
| 5,153,352 | 10/1992 | Norbeck | 560/17 |
| 5,391,739 | * 2/1995 | Peet | 514/258 |
| 5,593,997 | * 1/1997 | Dow et al. | 514/258 |
| 5,646,152 | * 7/1997 | Bright et al. | 514/258 |

FOREIGN PATENT DOCUMENTS

| | | |
|---|---|---|
| 2430454 | 1/1976 | (DE) . |
| 104522 | 4/1984 | (EP) . |
| 287907 | 10/1988 | (EP) . |
| 496617 | 7/1992 | (EP) . |
| 1311787 | 11/1962 | (FR) . |
| 2073274 | 10/1971 | (FR) . |
| 58-208283 | 12/1983 | (JP) . |
| 94/13677 | * 6/1994 | (WO) . |

OTHER PUBLICATIONS

Tominaga, et al., *J. Heterocycl. Chem*; vol. 27, No. (3), pp. 775–783, (1990).
Grohe, Klaus, *Synthesis*; No. 10, pp. 645–647, (1975).
Poli, et al., "Synthesis and In Vitro Antifungal Activity of 6–trifluoromethylpyrazolo[3,4–d]pyrimidines", *Pestic.*
Hasan et al., CA 108: 75765K: (1987).
Deo et al., CA 109: 73841d: (1987).
Cheng et al., *Journal of Organic Chemistry*, 23, pp. 191–200, (1958).
Cheng et al., *Journal of Organic Chemistry*, 21, pp. 1240–1256, (1956).
Sutcliffe, et al., *Journal of Medicinal and Pharamaceutical Chemistry*, pp. 588–607, vol. 5, No. 1, (1962).
Seng et al., *Journal of Heterocyclic Chemistry*; vol. 19, pp. (1565–1567), (1982).
R. M. Freidinger, *Med. Res. Rev.*, 9, pp. 271–290 (1990).
Owen et al. *Pharmacology Reviews*, 43(4), 425–472 (1991).
Singh et al., *Proc. Nat'l. Acad. Sci., U.S.*, , pp. 1130–1133, (1991).
Hayashi et al., *Yakugaku Zasshi*, 97, pp. 1328–1333, (1977).
Huard et al., *Biocatalysis*, (6), pp. 201–210, (1992).
Rosenberg, et al., *Collection Czechoslovak Chem. Comm.*, (50), pp. 1507–1513, (1985).
Hamilton, et al., *J. Med. Chem.*, (26), pp. 1601–1606, (1983).
Cottann et al., Nucleic Acids Research, 11 (3), pp. 871–882, (1983).
Prabhakar et al., *Indian J. of Biochemistry and Biophysics*, 27, pp. 342–347, (1990).
Montero et al., *J. Het. Chem.*, 14, pp. 483–487, (1977).
Avila et al., *Comp. Biochem Physiol*, 83C, pp. 285–289, (1986).
Avila et al., *Comp. Biochem Physiol*, 83C, pp. 291–294, (1986).

* cited by examiner

*Primary Examiner*—John M. Ford
(74) *Attorney, Agent, or Firm*—Peter C. Richardson; Paul H. Ginsburg; Seth H. Jacobs

(57) ABSTRACT

A compound of the formula:

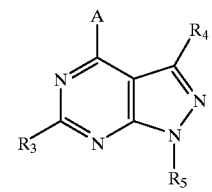

and the pharmaceutically acceptable acid addition salts thereof, wherein

A is $NR_1R_2$, $CR_1R_2R_{11}$, or $C(=CR_1R_{12})R_2$, $NHCR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$ or $C(O)R_2$;

wherein the rest of the variables are herein below defined, used for inflammatory disorders.

17 Claims, No Drawings

PYRAZOLOPYRIMIDINES AS CRF ANTAGONISTS

This application is a continuation of application Ser. No. 08/481,413, filed Jun. 15, 1995, now abandoned, which is a 35 U.S.C. §371 filing of PCT/US93/11333, filed Nov. 26, 1993, which is a continuation-in-part of application Ser. No. 07/992,229, filed Dec. 17, 1992 abandoned.

This invention relates to pyrazolopyrimidines, pharmaceutical compositions containing them, and their use in the treatment of stress-related and other diseases. The compounds have corticotropin-releasing factor (CRF) antagonist activity.

CRF antagonists are mentioned in U.S. Pat. No. 4,605,642 and 5,063,245 referring to peptides and pyrazolinones, respectively. The importance of CRF antagonists is set out in the literature, e.g. as discussed in U.S. Pat. No. 5,063,245, which is incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are considered effective in the treatment of a wide range of diseases including stress-related illnesses, such as stress-induced depression, anxiety, and headache; abdominal bowel syndrome; inflammatory diseases; immune suppression; Alzheimer's disease; gastronintestinal diseases; anorexia nervosa; hemorrhagic stress; drug and alcohol withdrawal symptoms; drug addition, and fertility problems.

Certain substituted pyrazolopyrimidines have been described in the past. For instance, European Patent Publication 496,617 refers to adenosine kinase inhibitors among which are 1-ribofuranosylpyrazolopyrimidines and 1-(substituted ribofuranosyl)pyrazolopyrimidines. U.S. Pat. No. 4,904,666 refers to pyrazolopyrimidines having 1-tetrahydrofuranyl or 1-tetrahydropyranyl substituents. Senga et al, J. Heterocyclic Chem., 19, 1565 (1982) refers to certain pyrazolopyrimidines having xanthine oxidase inhibitory acitivity. Other pyrazolopyrimidines are mentioned in U.S. Pat. Nos. 2,965,643 and 3,600,389.

The present invention relates to a pyrazolopyrimidine compound of the formula

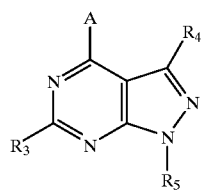

I and the pharmaceutically acceptable acid addition salts thereof, wherein

A is $NR_1R_2$, $CR_1R_2R_{11}$, $C(=CR_2R_{12})R_1$, $NHCR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$ or $C(O)R_2$;

$R_1$ is hydrogen, or $C_1$–$C_6$ alkyl which may contain one or two double or triple bonds or which may be substituted by one or two substituents $R_6$ independently selected form the group consisting of hydroxy, fluoro, chloro, bromo, iodo, $C_1$–$C_5$ alkoxy,

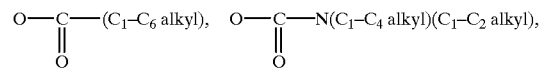

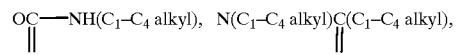

$SO_2(C_1$–$C_4$ alkyl), SH, CN, $NO_2$, $SO(C_1$–$C_4$ alkyl), $SO_2NH(C_1$–$C_4$ alkyl), $SO_2N(C_1$–$C_4$ alkyl)$(C_1$–$C_2$ alkyl), wherein said $(C_1$–$C_6)$ alkyl may have one or two double or triple bonds;

$R_2$ is $C_1$–$C_{12}$ alkyl, aryl or $(C_1$–$C_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or $(C_1$–$C_6$ alkylene) cycloalkyl, wherein said cycloalkyl may have one or two or O, S or N—Z wherein Z is hydrogen, $C_1$–$C_4$ alkyl, benzyl, or $C_1$–$C_4$ alkanoyl, wherein each one of the above groups may be substituted independently by from one to three of chloro, fluroro, or $(C_1$–$C_4)$alkyl, or one of hydroxy, bromo, iodo, $C_1$–$C_6$ alkoxy,

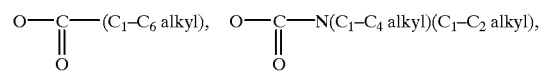

$S(C_1$–$C_6$ alkyl), $NH_2$, $NH(C_1$–$C_2$ alkyl), $N(C_1$–$C_2$ alkyl)$(C_1$–$C_4$ alkyl)

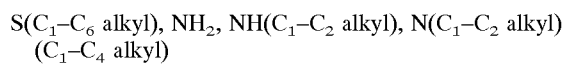

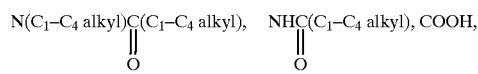

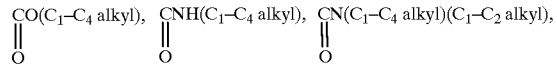

SH, CN, $NO_2$, $SO(C_1$–$C_4$ alkyl), $SO_2(C_1$–$C_4$ alkyl), $SO_2NH(C_1$–$C_4$ alkyl), $SO_2N(C_1$–$C_4$ alkyl)$(C_1$–$C_2$ alkyl), and wherein said $C_1$–$C_{12}$ alkyl or $C_1$–$C_{10}$ alkylene may have one to three double or triple bonds; or $NR_2R_2$ or $CR_1R_2R_{11}$ may form a saturated 4- to 8-membered ring optionally having one or two or O, S or N—Z wherein Z is hydrogen, $C_1$–$C_4$ alkyl, benzyl or $C_1$–$C_4$ alkanoyl;

$R_3$ is hydrogen, $C_1$–$C_6$ alkyl, fluoro, chloro, bromo, iodo, hydroxy, amino, $O(C_1$–$C_6$ alkyl), $NH((C_1$–$C_6$ alkyl)), $N(C_1$–$C_4$ alkyl)$(C_1$–$C_2$ alkyl), SH, $S(C_1$–$C_4$ alkyl), $SO(C_1$–$C_4$ alkyl), or $SO_2(C_1$–$C_4$ alkyl), wherein said $C_1$–$C_4$ alkyl and $C_1$–$C_6$ alkyl may have one or two double or triple bonds and may be substituted by from 1 to 3 substituents $R_7$ independently selected frothier group consisting of hydroxy, amino, $C_1-C_3$ alkoxy, dimethylamino, diethylamino, methylamino, ethylamino,

fluoro, chloro or $C_1-C_3$ thioalkyl;

$R_4$ is hydrogen, $C_1-C_6$ alkyl, fluoro, chloro, bromo, iodo, $C_1-C_6$ alkoxy, amino, $NH(C_1-C_6$ alkyl), $N(C_1-C_6$ alkyl) $(C_1-C_2$ alkyl), $SO_n(C_1-C_6$ alkyl), wherein n is 0, 1 or 2, cyano, hydroxy, carboxy, or amido, wherein said $C_1-C_6$ alkyls may be substituted by one to three of hdyroxy, amino, carboxy, amido,

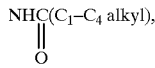

$NH(C_1-C_4$ alkyl), $N(C_1-C_4$ alkyl)$(C_1-C_2$ alkyl),

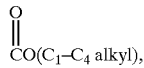

$C_1-C_3$ alkoxy, $C_1-C_3$ thioalkyl, fluoro, bormo, chloro, iodo, cyano or nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, tetrazolyl, or 3- to 8-membered cycloalkyl or 9- to 12-membered bicycloalkyl, optionally having one or two of O, S or N—Z wherein Z is hydrogen, $C_1-C_4$ alkyl, $C_1-C_4$ alkanoyl, phenyl or benzyl, wherein each one of the above groups may be substituted independently by from one to three of fluoro, chloro, bromo, formyl, $C_1-C_6$ alkyl, $C_1-C_6$ alkoxy, or trifluoromethyl, or one of hydroxy, iodo, cyano, nitro, amino, cycloproyl, $NH(C_1-C_4$ alkyl), $N(C_1-C_4$ alkyl) $(C_1-C_2$ alkyl), $COO(C_1-C_4$ alkyl), $CO(C_1-C_4$ alkyl), $SO_2NH(C_1-C_4$ alkyl), $SO_2N(C_1-C_4$ alkyl)$(C_1-C_2$ alkyl), $SO_2NH_2$, $NHSO_2((C_1-C_4$ alkyl), $S(C_1-C_6$ alkyl), $SO_2(C_1-C_6$ alkyl), wherein said $C_1-C_4$ alkyl and $C_1-C_6$ alkyl may have one double or triple bond and may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO $((C_1-C_2alkyl)$, cyano, or $CO(C_1-C_2$ alkyl; and $R_{12}$ is hydrogen or $C_1-C_5$ alkyl; with the following provisos:

(a) A is not straight chain $C_1-C_{12}$ alkyl;
(b) $R_5$ is not a sugar group;
(c) when $R_3$ and $R_4$ are hydrogen and $R_5$ is chlorophenyl, then A is not NH—CH(CH$_3$)—(CH$_2$)$_3$—N(C$_2$H$_5$)$_2$;
(d) when $R_3$ and $R_4$ are hydrogen and A is $NR_1R_2$ wherein $R_1$ is $C_3-C_7$ cycloalkyl, and $R_2$ is $C_2-C_6$ alkenyl, phenyl-$(C_1-C_6$ alkylene) or hetero-$(C_1-C_6$ alkylene) wherein the hetero radical is furyl, thienyl or pyridinyl, and wherein said pehnyl may be substituted by fluoro, chloro, bromo or iodo, then $R_5$ is not tetrahydrofuranyl or tetrahydropyranyl;

(e) when $R_3$ is methoxy, methylthio, or methylsulfonyl, $R_4$ is hydrogen, and $R_5$ is tetrahydrofuranyl or tetrahydropyranyl, then A is not $NH(C_1-C_2$ alkyl), morpholinyl, hdyrazino, or $NHC_2H_4C_6H_5$ the phenyl of which may be substituted by one methyl or two methoxy;

(f) when $R_3$ is hydrogen, $C_1-C_6$ alkyl, hydrazino, chloro, bromo, SH, or S $(C_1-C_4$ alkyl), $R_4$ is hydrogen and $R_5$ is $C_3-C_8$ cycloalkyl, then A is not hydrazino, $NH(C_1-C_2$ alkyl) or $N(C_1-C_6$ alkyl)$(C_1-C_{12}$ alkyl);

(g) when $R_3$ and $R_4$ are hydrogen and A is $NH(CH_2)_m$COOH wherein m is 1–12, then $R_5$ is not pehnyl substituted by one of fluoro, chloro, bromo or iodo;

(h) when $R_3$ is hydrogen, hydroxy, methythio, chloro or NHbenzyl, $R_4$ is hydrogen, and $R_5$ is chlorophenyl or bromophenyl, then A is not $NH(C_1-C_{12}$ alkyl), NHallyl, or $N((C_1-C_6$ alkyl) $(C_1-C_{12}$ alkyl), wherein said $C_1-C_{12}$ alkyl may be substituted by $NC_2H_5$, or NH benzyl which may be substituted by one or two bromo, chloro, fluoro, $NC_2H_5$ phenyl or morpholinopropyl;

(i) when $R_3$ and $R_4$ are hydrogen and $R_5$ is nitrophenyl, then A is not $NHR_2$ wherein $R_2$ is $C_1-C_{12}$ alkyl which may be substituted by two hydroxy, or $R_2$ is phenyl or benzyl;

(j) when $R_3$ is chloro or $O(C_1-C_6$ alkyl), $R_4$ is hydrogen, and A is $NR_1R_2$ wherein $R_1$ and $R_2$ are independently hydrogen or $C_1-C_6$ alkyl, then $R_5$ is not chlorophenyl; and (k) when $R_3$ is hydrogen, A is benzyl or phenethyl, and $R_4$ is fluoro, chloro, bromo or iodo, then $R_5$ is not 5'-deoxy-ribofuranosyl or 5'-amino-5'-deoxy-ribofuranosyl.

Preferred compounds of the formula I of the invention are those wherein $R_1$ is $C_1-C_4$ alkyl, $(C_2-C_4$ alkylene)$O(C_1-C_4$ alkyl), or $C_2-C_4$ hydroxyalkyl; those wherein $R_2$ is $C_1-C_5$ alkyl, benzyl, phenylethyl, or benzyl substituted by one or two of chloro, fluoro, methyl, ethyl, methoxy, ethoxy or t-butyl, or by one of trifluoromethyl; (2-thienyl)methyl; (2-thienyl)ethyl; (2-furanyl)methyl; 2-(4-chlorothienyl) methyl; (2-benzofuranyl)methyl; (2-benzothienyl)methyl; (2-thiazolyl)methyl; or (2-benzothiazolyl)methyl; those wherein $R_1$ is $C_1-C_4$ alkyl, $C_2-C_4$ hydroxyalkyl or $(C_2-C_4$ alkyl)-O-$(C_1-C_2$ alkyl); those wherein $R_3$ is hydrogen, methyl, ethyl, methoxy, fluoro or chloro; those wherein $R_4$ is mehtylthio, methylsulfonyl, methylsulfinyl, hydrogen, methyl, ethyl, or n-propyl, and those wherein $R_5$ is phenyl substituted by two or three substituents.

More specific compound of the formula I are those wherein a is $NR_1R_2$, $NHCHR_1R_2$, or $OCHR_1R_2$, wherein $R_1$ is $C_1-C_6$ alkyl, which may be substituted by one of hydroxy, fluoro or $C_1-C_2$ alkoxy, and may contain one double or triple bond, and $R_2$ is benzyl or $C_1-C_5$ alkyl which may contain one double or triple bond, wherein said $C_1-C_6$ alkyl or the phenyl in said benzyl may be usbstituted by fluoro, $C_1-C_6$ alkyl, or $C_1-C_5$ alkoxy; and those wherein A is $CR_1R_2R_1$, wherein $R_1$ is $C_1-C_6$ alkyl which may be substituted by one $C_1-C_6$ alkoxy or hydroxy, $R_2$ is benzyl or $C_1-C_6$ alkyl wherein said $C_1-C_6$ alkyl or the phenyl in said benzyl may be substituted by one $C_1-C_6$ alkyl, $C_1-C_5$ alkoxy, fluoro, chloro or bromo, and $R_{11}$ is hydrogen or fluoro.

More specific compounds of the formula I include those wherein $R_2$ is $(C_1-C_4$ alkylene)aryl wherein said aryl is pehnyl, thienyl, benzofuranyl, furanyl, benzothienyl, thiazolyl, pyridyl or benzothiazolyl.

More specific compounds of the formula I further include those wherein $R_2$ is benzyl para-substituted by one of ethyl, t-butyl, methoxy, trifluoromethyl, nitro, fluoro chloro, or methyl.

Other more specific compounds of the formula I include those wherein $R_2$ is attached through a methylene or ethylene bridge to quinolyl, pyrrolyl, pyrrolidinyl, pyridyl, tetrahydropyranyl, cyclopropyl, piperidinyl, or benzyl-piperdinyl.

More specific compounds (I) further include those wherein $R_1$ or $R_2$ is $C_1$–$C_6$ alkyl which may be substituted by one of hydroxy, methoxy, ethoxy, chloro, fluoro, OC(O)CH$_3$, OC(O)NHCH$_3$, C(O)NH$_2$.

Other more specific compounds (I) include those wherein $R_2$ is $C_1$–$C_6$ alkyl substituted by two of methoxy or ethoxy, or one of COOC$_2$H$_5$, methylthio, or phenyl.

Other more specific compounds (I) include those wherein A is $NR_1R_2$ or $CHR_1R_2$ in which $R_1$ and $R_2$ are taken together with N or CH to form a 5- or 6-membered ring having one more nitrogen, sulfur, and/or one oxygen, e.g. pyrrolidinyl, pyrroll, pyrazolyl, imidazolyl, oxazoly, thiazolyl, isoxazoly, thiadiazolyl, oxadiazolyl, pyridyl, pyrazinyl or pyrimidyl.

Other more specific compounds (I) includes those wherein A is $NHCHR_1R_2$ or $OCHR_1R_2$ in which $CHR_1R_2$ is a 5- or 6-membered ring which may contain one oxygen or sulfur, e.g. tetrahydrofuranyl, tetrahydrothiafuranyl and cyclopentanyl.

Most preferred compounds of the formula I include

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amino;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-cyclopropylmethyl -[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methyloxy-3-methylsulfanyl-1-(2,4,6-trichlorophenyl)-1H-pyrazolo[3,4-d]pyrimidin-4-yl]-amine;

propyl-ethyl-[3,6-diemthyl-1-(2,4,6-trimethylphenyl)-1H-pyrazolo[3,4-d]pyrimidin-4-yl]-amine;

4-(1-ethyl-propyl)-6-methyl-3-methylsuflanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1-ol;

[3,6-dimethyl-1-(2,4,6-trimethylphenyl)-1H-pyrazolo[3,4-d]pyrimidin-4-yl]-(1-methylpropyl)amine; and 4-(1-methoxymethylpropoxy)-3,6-dimethyl-1-(2,4,6-trimethylphenyl)-1H-pyrazolo[3,4-d]pyrimidine.

The invention also relates to a pharmaceutical composition for the treatment of illnesses induced or facilitated by conrticortropin releasing factor which comprises a compound of the formula I as defined above in an amount effective in the treatment of said illnesses, and a pharmaceutically acceptable carrier, and a pharmaceutical composition for the treatment of inflammatory disorders, such as arthritis, asthma and allergies; anxiety; depression; fatigue syndrom; headache; pain; caner; irritable bowel syndrome, including Chrohn's disease, spastic colon and irritable colon; immune dysfunciton; human immunodefiency virus (HIV) infections; neurodegenerative diseases such as Alzheimer's disease; gstrointestinal disease; eating disorders such as anorexia nervosa; hemorrhagic stress; drug and alcohol withdrawal symptoms; drug addiction; stress-induced psychotic episodes; and fertility problems, which comprises a compound of the formula I as defined above in an amount effective in the treatment of said disorders, and a pharmaceutically acceptable carrier. Preferred compositions of the invention are those containing preferred compounds of formula I as described above.

The invention further relates to a method for the treatment of illnesses induced or facilitated by corticotropin releasing factor by administering to a subject in need of such treatment a compound of formula I as defined above in an amount effective in such treatment, and a method for the treatment of inflammatory disorders, such as arthritis, asthma and allergies; anxiety; depression; fatigue syndrome; headache; pain; cancer; irritable bowel syndrome, including Chrohn's disease, spastic colon and irritable colon; immune dysfunction; human immunodefiency virus (HIV) infections; neurodegenerative diseases such as Alzheimer's disease; gastrointestinal diseases; eating disorders such as anorexia nervosa; hemorrhagic stress; drug and alcohol withdrawal symptoms; drug addiction; stress-induced psychotic episodes; and fertility of such treatment a compound of formula I as defined above in an amount effective in such treatment. Preferred methods of the invention are those administering a preferred compound of the formula I as described above.

Although $R_5$ includes cycloalkyl and bicycloalkyl containing oxygen atoms in the rings and hydroxyl and hydroxymethyl substituents on the rings, the compounds of formula I do not include sugar groups $C_nH_{2n-1}O_{n-1}$, such as $Ch_5H_9O_4$ (ribofuranosyl) and $C_6H_{11}O_5$ (ribopyranosyl), which have more than two hydroxy groups directly or indirectly attached to the ring or rings in the sugar group.

Whenever reference is made to alkyl, this includes straight and branched chain alkyl, unless otherwise indicated.

Whenever reference is made herein to 3-to 8-membered cycloakyl or 9- to 12-membered bicycloakyl containing one to three of O, S or N—Z, it is understood that the oxygen and sulfur ring atoms are not adjacent to each other. The three membered cycloalkyl has just one O, S or N—Z. An example of a six-membered cycloalkyl having O and N is morpholinyl.

Whenever $R_2$ or $R_5$ is a heterocyclic group, the attachment of the group is through a carbon atom.

Whenever reference is made herein to $C_1$–$C_4$ alkyl or $C_1$–$C_6$ alkyl which "may contain one or two double or triple bonds" in the definitions of $R_1$, $R_2$ and $R_3$, it is understood that at lest two carbons are present in the alkyl for one double or triple bond, and at least four carbons for two double and triple bonds.

Whenever an alkoxy group, e.g. in the definitions of $R_1$ and $R_2$, may have a double or triple bond, it is understood that such double or triple bond is not directly attached to the oxygen.

The compounds of formula I wherein A is $NR_1R_2$, $NHCR_1R_2R_{11}$, $OCR_1R_2R_{11}$, $SCR_1R_2R_{11}$ or $NHNR_1R_2$, and $R_2$ is hydrogen, $C_1-C_6$ alkyl or chloro (hereafter $R_9$) may be prepared by reaction of a compound of the formula

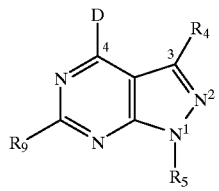
II wherein D is Cl, and $R_4$, $R_5$ and $R_6$ are as defined above with reference to formula I, with a compound of the formula AH wherein A is as defined immediately above. The reaction is carried out in a solvent in the presence of a base at a temperature of between about 0° to about 150° C. Suitable solvents are organic solvents such as acetonitrile, dimethylsulfoxide, acetone, $C_2-C_{15}$ alkyl alcohol, tetrahydrofuran, chloroform, benzene, xylene or tuluene, preferably acetonitrile or dimethylsulfoxide.

When A is $NR_1R_2$, $NHNR_1R_2$, or $NHCR_1R_2R_{11}$, an excess of AH is used. Other bases such as potassium carbonate or tri-$(C_1-C_6)$alkyl amine may be used instead. The reaction is carried out at a temperature of about 75° to 150° C. When the reaction is carried out in the presence of a base, such as sodium hydride or potassium $C_1-C_4$ alkoxide, a molar equivalent of the amine is used. When A is $OCR_1R_2R_{11}$ or $SCR_1R_2R_{11}$, a base which is capable of deprotonation of AH may be used, such as an alkali metal hydride such as sodium or potassium hydride, or an organometallic base such as sodium diisopropylamide, sodium bis(trimethylsily)amide, lithium diisopropylamide, lithium bis(trimethylsily)amide, sodium $C_1-C_4$ alkoxyde or n-butylthium. The solvent used is dry tetrahydrofuran, dimethylsulfoxide, methylene chloride, or tuluene, and the reaction temperature is between about -78° C. and the reflux temperature of the reaction mixture, preferably 0° C to 80° C.

The compounds of formula II wherein D is chloro may be prepared by reacting the corresponding 4-hydroxy compound of formula III (not shown) with a molar excess of phosphorus oxychloride or thionyl chloride at temperatures between about 60 to 140° C., conveniently at the reflux temperature of the reaction mixture. When the reaction is carried out in a solvent, suitable solvents are halogenated alkanes, such as methylene chloride or chloroform. The reaction may be in the presence of a base such as N, N-diethylaniline, trimethylamine or potassium carobnate.

The compounds of the formula III as defined above may be prepared by reaction of a compound of the formula

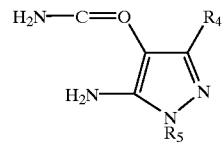
IV wherein $R_4$ and $R_5$ are as defined with reference to formula I, with a compound of the formula

(V) wherein $R_9$ is as defined above. This reaction is conveniently carried out in the absence of a solvent at temepratures between about 100° C. to 250° C.

The compounds of formulae IV and V are either readily available or may be prepared by conventional methods.

As depicted in Scheme 1, the compounds of formula I wherein $R_3$ is the groups other than $R_9$ (hereafter $R_{10}$) may be prepared by reacting a compound of the formula I wherein $R_3$ is chloro, having formula VIII in scheme 1, with a nucleophile of the formula $R_{10}H$ with or without an organic or inorganic base. Suitable bases include sodium, sodium hydride, and alkali metal hydroxide such as potassium hydroxide, and weaker bases such as potassium carbonate or triethylamine. The latter are generally used when $R_{10}H$ is alkanol, $C_1-C_6$ alkanethiol, an amine, e.g. $NH(C_1-C_6$ alkyl), or tetrahydrobutylammonium fluoride. Suitable solvents are dimethylsulfoxide, acetonitrile, $C_1-C_5$ alkyl alcohol, tetrahydrofuran, benzene, toluene or methylene chloride.

Scheme I

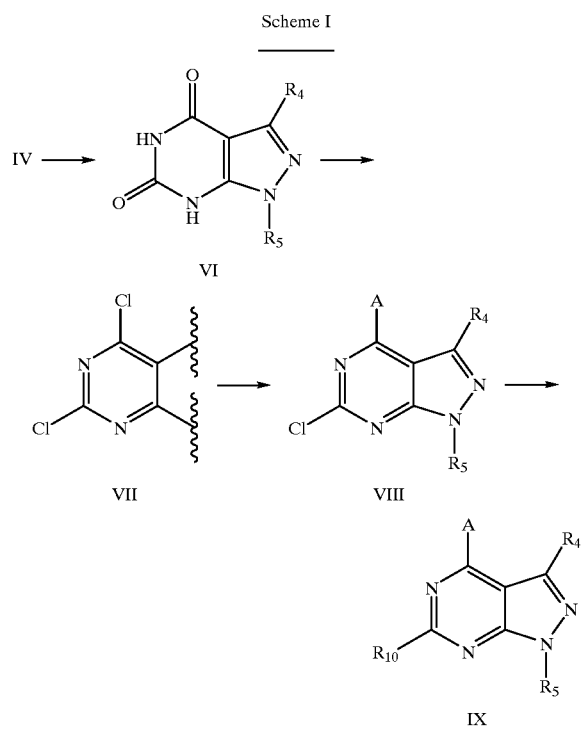

The compound of formula IV as defined above is reacted with an excess of urea at reflux temperature to form a compound of the formula VI. The compound of formula VII is formed on reaction of a compound VI with phosphorus oxychloride or thionyl chloride at temperatures between about 70° C. to 140° C. and conveniently the reflux temperature of the reaction mixture, in the optional presence of a base such as N,N-diethylaniline. The compound of formula VIII is formed on reaction of compound VII with AH under the same reaction conditions as described above for the reaction of compound II with AH.

The compounds of the formula I wherein A is $CR_1R_2R_{11}$ or $C(=CR_{12}R_{13})R_2$ may be prepared, as depicted in Scheme 2 below, from corresponding compounds of the formula II wherein $R_4$ and $R_5$ are as defined above, and $R_9$ is $R_3$ as defined with reference to formula I by reaction with a compound of the formula $CHR_1R_{14}R_{15}$ wherein $R_1$ is as defined with reference to formula I, and $R_{14}$ and $R_{15}$ are each independently $COO(C_1-C_2$ alkyl), $CO(C_1-C_2$ alkyl) or CN, to form the compound of formula IA. The reaction is carried out in the presence of a base such as sodium hydride, potassium $C_1-C_5$ alkoxide, sodium or lithium bis(trimethylsilyl) amide, and sodium or lithium diisopropylamide, in a reaction inert solvent such as dimethylsulfoxide, acetonitrile, $C_2-C_6$ alkyl alcohol, or N-methyl-pyrrolidone, preferably dimethylsulfoxide. The reaction is preferably carried out at elevated temperatures of about 100° C. to 180° C.

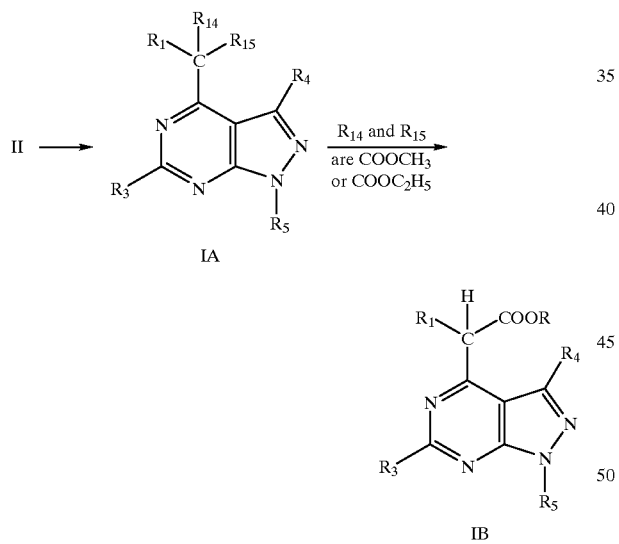

The compounds of formula IB may be prepared by reaction of those compounds of formula IA wherein $R_{14}$ and $R_{15}$ are each COOR wherein R is methyl or ethyl, by reaction with diisobutylaluminum hydride in a reaction inert solvent at temperatures of about −78° C. to 40° C., preferably about −20° to 25° C. Suitable solvents are toluene, benzene and tetrahydrofurane, preferably toluene.

The compounds of formula IB may be converted into corresponding compounds of the formula

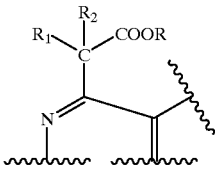

IC by reaction with a compound of the formula $R_2L$ wherein $R_2$ is as defined with reference to formula I, and L is a leaving group such as chloro, bromo, iodo, mesylate or tosylate, in the presence of a base and a reaction inert solvent at temperatures of about 0° to 50° C., preferably room temperature. Suitable solvents include dimethylsulfoxide, $C_2-C_6$ alkyl alcohol, tetrahydrofuran, methylene chloride and dioxane.

The compounds of the formulae

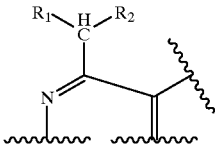

ID

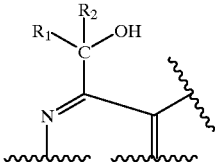

IE may be prepared from the corresponding compounds of formula IC by reaction with lithium iodide in a solvent such as dimethylformamide, dimethyl sulfoxide and dioxane at temperatures of about 50° C. to 200° C., preferably about 100° to 150° C. The reaction to form compound IE is in the presence of air.

When $R_2$ in above formula IE is a group of the formula $CHR_2R_{12}$, then the compounds of formula IE may be further converted to corresponding compounds of the formula

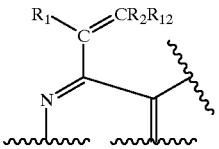

IF using the same reaction conditions as used for the conversion of compounds IC to ID.

The compounds of formula I wherein A is $CR_1R_2R_{11}$ or $C(=CR_2R_{12})R_1$ may be prepared as shown in Scheme 3.

The compounds of formula XIV may be prepared by reaction of the trialkoxy compound $R_4C(OR)_3$ wherein R is $C_1-C_2$ alkyl and $R_4$ is as defined with reference to formula I with the compound of formula XIII, wherein $R_2$ and $R_{11}$ may be replaced by $=CR_2R_{12}$, in the presence of acetic anhydride and in the optional presence of a solvent such as ethyl acetate, methylene chloride, chloroform, or toluene. The reaction is carried out at temperatures of about 30° C. to 150° C., preferably 80° C. to 120° C. The compound of formula XV is obtained by reacting the corresponding compound of formula XIV with a hydrazine of the formula $R_5NHNH_2$, wherein $R_5$ is as defined with reference to formula I, in a solvent such as a $C_1-C_4$ alkyl alcohol or acetonitrile at a temperature of about 60° to 120° C., preferably reflux temperature.

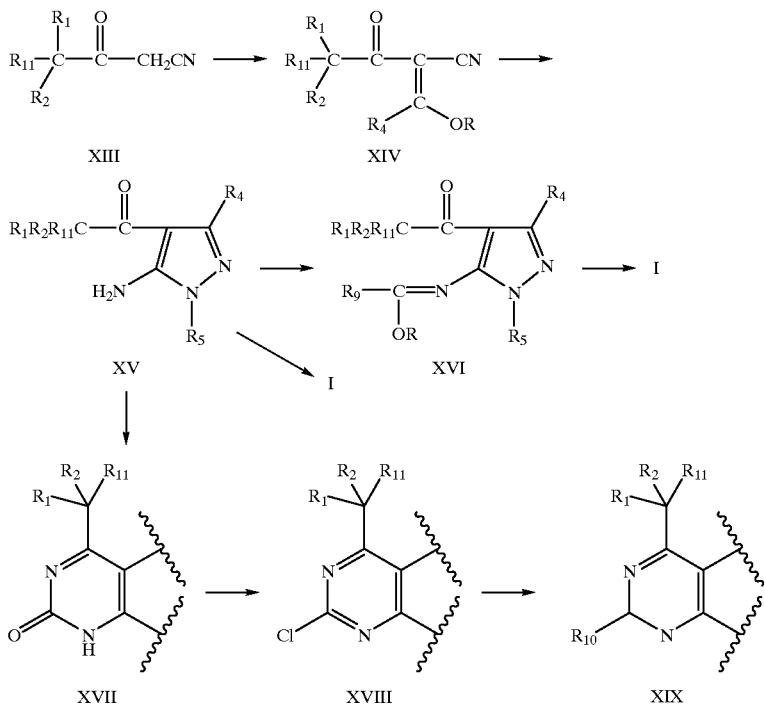

The compounds of formula I wherein A is $CR_1R_2R_{11}$ may be obtained by reacting the corresponding compound of formula XV with $R_9CONH_2$, wherein $R_9$ is hydrogen, $C_1-C_6$ alkyl or amino, in the presence of ammonium chloride by heating at reflux temperatures of about 240° C. Alternatively, the compound of formula XVI may be prepared from the corresponding compound of formula XV with $R_9C(OR)_3$ wherein R is $C_1-C_2$ alkyl using reaction conditions similar to those used for the preparation of compounds of the formula II from the compounds of formula III, as described above.

The compounds of formula XV may be reacted with an excess of urea at reflux temperatures to form a compound of the formula XVII. Conversion of compounds XVII to XVIII and XIX may be effected by the same procedure as in Scheme 1 for the conversion of compounds VII to VIII and IX, respectively.

The compounds of formula I wherein A is $CR_1R_2R_{11}$, $C(=C_2R_{12})R_1$, $CR_2R_{11}NHR_1$, $CR_2R_{11}SR_1$, or $C(O)R_2$, and $R_3$ is $R_9$ as defined above with reference to formula II, may be prepared as depicted in Scheme 4.

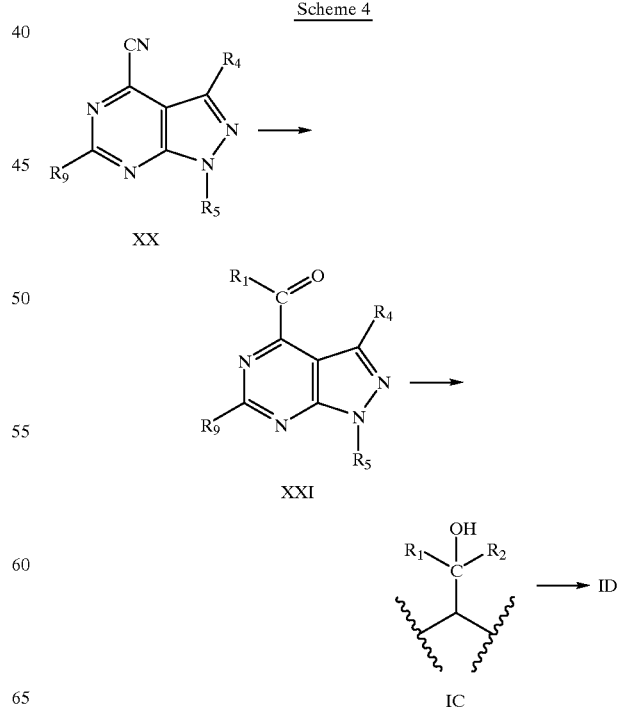

The compounds of formula XX, wherein $R_4$, $R_5$, and $R_9$ are as defined above, prepared by reacting the corresponding compound of formula II with potassium cyanide in dimethylsulfoxide, are reacted with a Grignard reagent containing group $R_1$ as defined above to form the compound of formula XXI. Further reaction of the compound of formula VII with a Grignard reagent containing group $R_2$ as defined above provides the compound of formula IC. Corresponding compounds of formula ID wherein B is $CR_1R_2R_{11}$ or $C(=CR_2R_{12})R_1$ may be prepared by conventional methods.

The compounds of formula I wherein group $R_1$, $R_2$, $R_3$, $R_4$ or $R_5$ contains a sulfoxy or a sulfinyl group may be obtained by oxidation of the corresponding sulfur compound, as is known by the skilled person.

When the compounds of the invention contain one or more chiral centers, it is understood that the invention includes the racemic mixture and the individual diastereomers and enantiomers of such compounds.

The pharmaceutically acceptable acid addition salts are prepared in a conventional manner by treating a solution or suspension of the free base of formula I with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The novel compound of the invention of formula I may be administered alone or in combination with pharmaceutically acceptable carriers, in either single or multiple, e.g. up to three, doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitable buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds of the present invention topically when treating inflammatory conditions of the skin and this may be done by way of creams, jellies, gels, pastes, and ointments, in accordance with standard pharmaceutical practice.

The effective dosage for the compound of formula I depends on the intended route of administration and other factors such as age and weight of the patient, as generally known to a physician. The dosage is also depends on the illness to be treated. The daily dosage will generally range from about 0.1 to 50 mg/kg of the body weight of the patient to be treated. For treatment of inflammatory diseases about 0.1 to about 100 mg/kg will be needed, and for Alzheimer's disease, about 0.1 to about 50 mg/kg, as well as for gastrointestinal diseases, anorexia nervosa, hemorrhagic stress, drug and alcohol withdrawal symptoms, fertility problems, etc.

The methods for testing the compounds of formula I for their CRF antagonist activity are as described in Endocrinology, 116, 1653–1659 (1985) and Peptides 10, 179–188 (1989), which determine the binding affinity of a test compound to a CRF receptor. The binding affinity for the compounds of formula I, expressed as $IC_{50}$ values, generally ranges from about 0.2 nanomolar to about 10 micromolar.

The following Examples illustrate the invention. The following abbreviations are used: Ph=phenyl, Me=ethyl, t-Bu=t.butyl, Et=ethyl, Pr=propyl.

Example 1

3-{(4-methylbenzyl)-[6-methyl-3-methylsulfanyl-1-(2,4,6-trichlorophenyl)-1H-pyrazolo[3,4-d]pyrimidin-4-yl]-amino}-propanol A mixture of 4-chloro-3-methylsulfanyl-6-methyl-1-(2,4,6-trichlorophenyl)-1H-pyrazolo[3,4-d]pyrimidine (788 mg, 2 mmol) and 3-(p-methylbenzyl)amino-1-propanol (716 mg, 4 mmol) in 10 ml of acetonitrile was heated at reflux for 4 hours. The mixture was cooled, quenched with water and dilute hydrogen chloride and extracted with ethyl acetate. The organic layer was washed with aqueous sodium bicarbonate and brine, separated, dried and concentrated to give 953 mg of the title compound as an off-white glass form. The material was purified through silica gel column chromatography using chloroform as eluent to give the title compound as a white glass form. $^1$H NMR (CDCl$_3$): 1.79 (m, 2H), 2.38 (s, 3H), 2.52 (s, 3H), 2.54 (s, 3H), 3.56 (t, 2H), 3.86 (t, 2H), 5.12 (s, 2H), 7.20 (s, 4H), 7.51 (s,2H) ppm. $^{13}$C NMR (CDCl$_3$): 16.20, 21.13, 25.53, 29.64, 43.51, 53.88, 58.24, 127.78, 128.77, 129.33, 133.51, 136.18, 137.41, 142.93, 159.13, 164.89 ppm. IR(KBr): 3350, 2935, 1540 cm$^{-1}$. Anal. calc. for 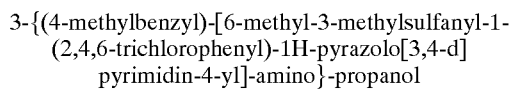 C, 53.69; H, 4.50; N, 13.04; found: C, 53.33, H, 4.44, N, 12.84.

Example 2

The following compounds were prepared starting with the appropriate amine and 4-chloro-3-methylsulfanyl-6-methyl-1-(2,4,6-trichlorophenyl)-1H-pyrazolo[3,4-d]pyrimidine and employing the procedure of Example 1.

TABLE 1

[Structure: 4-(NR₁R₂)-3-(SMe)-6-Me-1-(2,4,6-trichlorophenyl)-1H-pyrazolo[3,4-d]pyrimidine]

| NR₁R₂ | ¹H NMR (CDCl₃) ppm |
|---|---|
| PhCH₂N(CH₂)₂OH | 2.48(s,3H), 2.52(s,3H), 3.7–3.9 (m,4H), 5.14(s,2H), 7.2–7.4 (m,5H), 7.48(s,2H) |
| PhCH₂N(CH₂)₃OH | 1.80(m,2H), 2.52(s,3H), 2.54 (s,3H), 3.56(t,2H), 3.88(t,2H), 5.17(s,2H), 7.30–7.40(m,5H), 7.51(s,2H) |
| Ph(CH₂)₂N(CH₂)₃OH | 1.90(,2H), 2.49(s,3H), 2.63 (s,3H), 3.07(m,2H), 3.57(t,2H), 3.92(t,2H), 4.12(t,2H), 4.4 (brs,1H), 7.2–7.5(m,5H), 7.51 (s,2H) |
| p-Cl—PhCH₂N(CH₂)₃OH | 1.82(m,2H), 2.52(s,3H), 2.55 (s,3H), 3.57(q,2H), 3.86(s,2H), 5.12(s,2H), 7.2–7.4(m,4H), 7.51(s,2H) |
| p-O₂N—PhCH₂N(CH₂)₃OH | 1.88(m,2H), 2.50(s,3H), 2.53 (s,3H), 3.61(t,2H), 3.89(t,2H), 5.23(s,2H), 7.45–7.55(m,2H), 7.50(s,2H), 8.24(d,2H) |
| p-MeO—PhCH₂N(CH₂)₃OH | 1.71(m,2H), 2.49(s,3H), 2.52 (s,3H), 3.5(t,2H), 3.80(s,3H), 3.82(t,2H), 5.05(s,2H), 6.88 (d,2H), 7.20(d,2H), 7.5(s,2H) |
| p-F₃C—PhCH₂N(CH₂)₃OH | 1.82(m,2H), 2.5(s,3H), 2.52 (s,3H), 3.55(m,2H), 3.85(t,2H), 5.15(s,2H), 7.4(d,2H), 7.5 (s,2H), 7.6(d,2H) |
| p-Cl—PhCH₂N(CH₂)₄OH | 1.45–1.70(m,2H), 1.70–1.90 (m,2H), 2.49(s,3H), 2.59(t,3H), 3.62–3.75(m,4H), 5.04(s,2H), 7.2–7.4(m,4H), 7.50(s,2H) |
| p-t-Bu—PhCH₂N(CH₂)₃OH | 1.34(s,9H), 1.75–1.85(m,2H), 2.51(s,3H), 2.55(s,3H), 3.50–3.51(m,2H), 3.86(t,2H), 5.14 (s,2H), 7.15–7.45(m,4H), 7.51 (s,2H) |
| o-Me—PhCH₂N(CH₂)₃OH | 1.8(m,2H), 2.2(s,3H), 2.45 (s,3H), 2.55(s,3H), 3.6(t,2H), 3.95(t,2H), 5.1(s,2H), 7.1–7.3(m,4H), 7.45(s,2H) |
| 2,5-di-Me—PhCH₂N(CH₂)₃OH | 1.75(m,2H), 2.20(s,3H), 2.25 (s,3H), 2.45(s,3H), 2.50(s,3H), 3.52(t,2H), 3.90(t,2H), 5.04 (s,2H), 6.90(s,1H), 6.92–7.10 (m,2H), 7.45(s,2H) |
| 2,4,6-tri-Me—PhCH₂N(CH₂)₃OH | 1.59(m,2H), 2.2(s,6H), 2.28 (s,3H), 2.50(s,3H), 2.60(s,3H), 3.48(t,2H), 3.68(t,2H), 4.4 (brs,1H), 5.1(s,2H), 6.82 (s,2H), 7.50(s,2H) |
| o-F—PhCH₂N(CH₂)₃OH | 1.82(m,2H), 2.45(s,3H), 2.46 (s,3H), 3.56(t,2H), 3.88(t,2H), 5.20(s,2H), 7.0–7.3(m,4H), 7.47(s,2H) |
| p-Et—PhCH₂N(CH₂)₃OH | 1.23(t,3H), 1.7–1.85(m,2H), 2.48 (s,3H), 2.51(s,3H), 2.64(q,2H), 3.5–3.6(m,2H), 3.8–3.95(m,2H), 5.1(s,2H), 7.1–7.3(m,4H), 7.48(s,2H) |
| p-F—PhCH₂N(CH₂)₃OH | 1.8(m,2H), 2.50(s,3H), 2.58 (s,3H), 3.6(t,2H), 3.88(t,3H), 5,1(s,2H), 7.0–7.3(m,4H), 7.5(s,2H) |
| 2-thienyl-CH₂N(CH₂)₃OH | 1.9(m,2H), 2.55(s,3H), 2.60 (s,3H), 3.6(t,2H), 3.93(t,2H), 5.25(s,2H), 7.0(dd,1H), 7.05 (m,1H), 7.28(dd,1H), 7.48(s,2H) |
| 2-thienyl-(CH₂)₂N(CH₂)₃OH | 1.95(m,2H), 2.50(s,3H), 2.65 (s,3H), 3.35(m,2H), 3.62(t,2H), 4.0(t,2H), 4.15(m,2H), 6.9 (m,2H), 7.15(d,1H), 7.5(s,2H) |
| Ph(CH₂)₂NCH₂CH(OEt)₂ | 1.1–1.3(m,6H), 2.47(s,3H), 2.63 (s,3H), 3.05(t,2H), 3.5–3.65 (m,2H), 3.65–3.82(m,2H), 3.89 (d,2H), 4.22(t,2H), 4.82(t,1H), 7.1–7.4(m,5H), 7.50(s,2H) |
| 2-quinolinyl-CH₂N(CH₂)₃OH | 2.05(m,2H), 2.49(s,3H), 2.54 (s,3H), 3.65(t,2H), 3.99(t,2H), 5.52(s,2H), 7.51(s,2H), 7.52–7.9(m,4H), 8.21(t,2H) |
| 2,6-di-Cl—PhCH₂N(CH₂)₃OH | 1.58(m,2H), 2.54(s,3H), 2.67 (s,3H), 3.52(t,2H), 3.84(t,2H), 5.40(s,2H), 7.2–7.4(m,3H), 7.52(s,2H) |
| thiazolidinyl | 2.55(s,3H), 2.65(s,3H), 3.15 (t,2H), 4.25(t,2H), 5.0(s,2H), 7.5(s,2H) |
| p-Cl—PhCH₂N(CH₂)₂COOEt | 1.22(t,3H), 2.50(s,3H), 2.58 (s,3H), 2.76(t,2H), 3.96(t,2H), 4.10(q,2H), 5.08(s,2H), 7.2–7.4(m,4H), 7.51(s,2H) |
| 1-pyrrolidinyl-(CH₂)₂N(CH₂)₂OH | 1.7(m,4H), 2.0(m,2H), 2.45 (s,3H), 2.62(s,3H), 2.65(m,4H), 2.95(t,2H), 3.6(t,2H), 4.0 (m,4H), 7.48(s,2H) |
| p-MePhCH₂N(CH₂)₃SMe | 2.0(m,2H), 2.1(s,3H), 2.35 (s,3H), 2.5(s,3H), 2.6(s,3H), 3.75(m,2H), 5.05(s,2H), 7.18 (q,4H), 7.5(s,2H) |
| PhCH₂-(2-imidazolinyl) | 2.54(s,3H), 2.64(s,3H), 4.05 (m,2H), 4.2–4.3(m,4H), 7.05–7.25(m,5H), 7.50(s,2H) |
| PhCH₂-(2-hydroxy-imidazolidinyl) | 2.47(s,3H), 2.68(s,3H), 3.55 (s,2H), 3.5–3.65(m,2H), 3.8 (m,2H), 6.15(brs,1H), 6.30(brs,1H), 7.15–7.32(m,5H), 7.5(s,2H) |
| 3-quinolinyl-CH₂NCH₂N(CH₂)₃OH | 1.85(m,2H), 2.50(s,3H), 2.52 (s,3H), 3.60(t,2H), 3.89(t,2H), 5.13(s,2H), 7.25(d,2H), 7.50 (s,2H), 8.59(d,2H) |
| 2-quinolinyl-CH₂N(CH₂)₃OH | 1.88(m,2H), 2.50(s,3H), 2.51 (s,3H), 3.60(t,2H), 3.95(t,2H), 5.27(s,2H), 7.25(m,1H), 7.32 |

TABLE 1-continued

| NR₁R₂ | ¹H NMR (CDCl₃) ppm |
|---|---|
|  | (d,1H), 7.50(s,2H), 7.70(t,1H), 8.62(d,1H) |
| MeCON(CH₂)₂OH | 2.1(s,3H), 2.5(s,3H), 2.68 (s,3H), 3.95(q,2H), 4.35(t,2H), 6.15(t,1H), 7.47(s,2H) |
| imidazolyl | 2.68(s,3H), 2.75(s,3H), 7.33 (s,1H), 7.57(s,2H), 7.92(s,1H), 8.69(s,1H) |
| 2-pyridyl-CH₂N(CH₂)₃OMe | 2.0–2.1(m,2H), 2.45(s,3H), 2.56 (s,3H), 3.25(s,3H), 3.44(t,2H), 3.90(t,2H), 5.2(s,2H), 7.18 (m,1H), 7.30(m,1H), 7.50(s,2H), 7.64(t,1H), 8.58(m,1H) |
| 2-furanyl-CH₂—N(CH₂)₂—SH | 2.48(s,3H), 2.62(s,3H), 2.80 (m,2H), 3.90(t,2H), 5.03(s,2H), 6.32(s,2H), 7.36(s,1H), 7.47 (s,2H) |
| 3-pyridyl-CH₂N(CH₂)₃OH | 1.85(m,2H), 2.49(s,3H), 2.53 (s,3H), 3.59(t,2H), 3.86(t,2H), 5.13(s,2H), 7.3–7.4(m,1H), 7.48(s,2H), 7.71(m,1H), 8.55–8.62(m,2H) |
| 2-(4-chlorothienyl)-(CH₂)₂N(CH₂)₃OH | 1.90(m,2H), 2.54(s,3H), 2.62 (s,3H), 3.63(t,2H), 3.90(t,2H), 5.07(s,2H), 6.76(d,1H), 6.84 (d,1H), 7.49(s,2H) |
| 4-(1-benzylpiperidinyl)-CH₂N(CH₂)₃OH | 1.3–1.5(m,2H), 1.5–1.75(m, 2H), 1.75–2.1(m,5H), 2.42 (s,3H), 2.62(s,3H), 2.8–3.0(m,2H), 3.5(s,2H), 3.55(t,2H), 3.80 (d,2H), 3.89(t,2H), 7.2–7.4 (m,5H), 7.48(s,2H) |
| 2-benzofuranyl-CH₂N(CH₂)₃OH | 1.87(m,2H), 2.54(s,3H), 2.59 (s,3H), 3.62(t,2H), 4.01(t,2H), 5.31(s,2H), 6.70(s,1H), 7.2–7.4(m,2H), 7.52(s,2H), 7.4–7.6(m,2H) |
| 2-furanyl-CH₂N(CH₂)₃OH | 1.77(m,2H), 2.50(s,3H), 2.61 (s,3H), 3.55(t,2H), 3.90(t,2H), 4.51(brs,1H), 5.13(s,2H), 6.36 (m,2H), 7.41(m,1H), 7.50(s,2H) |
| 2-furanyl-NH | 2.55(s,3H), 2.67(s,3H), 4.88 (d,2H), 6.19(t,1H), 6.37(m,2H), 7.42(d,1H), 7.51(s,2H) |
| 2-benzofuranyl-CH₂N(CH₂)₂OH | 2.57(s,3H), 2.61(s,3H), 3.86 (t,2H), 4.01(t,2H), 5.32(s,2H), 6.77(sm1H), 7.2–7.4(m,2H), 7.52(s,2H), 7.45–7.60(m,2H) |
| p-Cl—PhCH₂N(CH₂)₂OH | 2.5(s,3H), 2.55(s,3H), 3.8 (s,4H), 5.1(s,2H), 7.2–7.4 (m,4H), 7.5(s,2H) |
| 2-benzothienyl-CH₂N(CH₂)₃OH | 1.90(m,2H), 2.50(s,3H), 2.58 (s,3H), 3.6(t,2H), 3.95(t,2H), 5.3(s,2H), 7.2–7.4(m,3H), 7.5(s,2H), 7.7–7.85(m,2H) |
| 3-quinolinyl-CH₂N(CH₂)₃OH | 1.87(m,2H), 2.49(s,3H), 2.51 (s,3H), 3.60(t,2H), 3.92(t,2H), 5.30(s,2H), 7.49(s,2H), 7.57 (m,1H), 7.73(m,1H), 7.81(m,1H), 8.08(d,1H), 8.14(d,1H), 8.93(d,1H) |
| HN(CH₂)₃OH | 1.85(m,2H), 2.50(s,3H), 2.68 (s,3H), 3.65(t,2H), 3.85(q,2H), 6.15(brs,1H), 7.50(s,2H) |
| PhCH₂N-n-Pr | 0.9(t,3H), 1.75(m,2H), 2.48 (s,3H), 2.60(s,3H), 3.79 (t,2H), 5.1(s,2H), 7.25–7.4(m,5H), 7.50(s,2H) |
| p-Cl—PhCH₂N(CH₂)₂COOH | 2.49(s,3H), 2.54(s,3H), 2.72 (t,2H), 3.88(t,2H), 5.07 (s,2H), 7.1–7.3(m,4H), 7.50(s,2H) |
| 2-tetrahydropyranyl-CH₂N(CH₂)₃OH | 1.2–2.0(m,8H), 2.5(s,3H), 2.6(s,3H), 3.2–4.2 (m,9H), 7.5(s,2H) |
| (p-methylbenzyl)-(2-furanylmethyl)amino | 2.28(s,3H), 2.44(s,3H), 2.50 (s,3H), 4.82(s,2H), 4.90(s,2H), 6.16(m,1H), 6.24(m,1H), 7.0–7.2(m,4H), 7.28(m, 1H), 7.40(s,2H) |
| 2-thiazolyl-CH₂N(CH₂)₃OH | 2.00(m,2H), 2.53(s,3H), 2.58 (s,3H), 3.63(t,2H), 3.97(t,2H), 5.36(s,2H), 7.32(d,1H), 7.48 (s,2H), 7.50(d,1H) |
| 2-benzothiazolyl-CH₂N(CH₂)₃OH | 2.6(s,3H), 3.67(t,2H), 4.05 (t,2H), 5.5(s,2H), 7.35–7.55 (m,2H), 7.5(s,2H), 7.85 (d,1H), 8.05(d,1H) |
| p-Me—PhCH₂N(CH₂)₃NH₂ | 1.7(brs,2H), 1.8(m,2H), 2.3 (s,3H), 2.44(s,3H), 2.52(s,3H), 2.68(m,2H), 3.71(t,2H), 5.0 (s,2H), 7.05–7.18(m,4H), 7,44(s,2H) |
| p-H₂N—PhCH₂N(CH₂)₃OH | 1.73(m,2H), 2.50(s,3H), 2.55 (s,3H), 3.55(t,2H), 3.82(t,2H), 5.0(s,2H), 6.7(d,2H), 7.05 (d,2H), 7.48(s,2H) |
| 3-benzothienyl-CH₂N(CH₂)₃OH | 1.8(m,2H), 2.48(s,3H), 2.52 (s,3H), 3.55(t,2H), 3.97(t,2H), 5.35(s,2H), 7.28(s,1H), 7.35–7.45(m,2H), 7.55(m,1H), 7.88 (m,1H) |
| p-Me—PhCH₂NCH₂CH(OH)CH₂OH | 2.37(s,3H), 2.51(s,3H), 2.55 (s,3H), 3.4–3.6(m,3H), 3.7–4.0(m,2H), 5.17(ABq,2H), 7.20 (s,4H), 7.51(s,2H) |
| NEt₂ | 1.33(t,4H), 2.46(s,3H), 2.65 (s,3H), 3.82(q,4H), 7.49(s,2H) |
| PhCH₂N(CH₂)₃F | 2.0–2.2(m,2H), 2.46(s,3H), 2.56 (s,3H), 3.78(m,2H), 4.50(dt, J=45 & 6 Hz), 5.08(s,2H), 7.23(s,5H), 7.46(s,2H) |
| PhCH₂N(CH₂)₃Cl | 2.1–2.2(m,2H), 2.47(s,3H), 2.57 (s,3H), 3.57(t,2H), 3.80(t,2H), 5.08(s,2H), 7.2–7.4 (m,5H), 7.48(s,2H) |
| n-BuN(CH₂)₂OH | 0.96(t,3H), 1.35–1.50(m, 2H), 1.7–1.8(m,2H), 2.45(s,3H), 2.64(s,3H), 3.80–3.97(m,6H), 5.71(s,1H), 7.48(s,2H) |

TABLE 1-continued

[Structure: 4-(NR₁R₂)-3-SMe-6-Me-1-(2,4,6-trichlorophenyl)-1H-pyrazolo[3,4-d]pyrimidine]

| NR₁R₂ | ¹H NMR (CDCl₃) ppm |
|---|---|
| EtN(CH₂)₂OH | 1.43(t,3H), 2.47(s,3H), 2.66(s,3H), 3.90–4.0(m,6H), 5.78(s,1H), 7.50(s,2H) |
| NMe₂ | 2.49(s,3H), 2.64(s,3H), 3.38(s,6H), 7.49(s,2H) |
| N(n-Bu)₂ | 0.97(t,6H), 1.3–1.5(m,4H), 1.65–1.82(m,4H), 2.46(s,3H), 2.64(s,3H), 3.73(t,4H), 7.49(s,2H) |
| CH₃(CH₂)₄N(CH₂)₂OH | 0.90(t,3H), 1.3–1.42(m,4H), 1.68–1.82(m,2H), 2.42(s,3H), 2.61(s,3H), 3.70–3.95(m,6H), 7.46(s,2H) |
| CH₃(CH₂)₄NCH₂CH₃ | 0.95(t,3H), 1.30(t,3H), 2.43(s,3H), 2.61(s,3H), 3.68(t,2H), 3.76(q,2H), 7.46(s,2H) |
| 2-pyrrolyl-CH₂N(CH₂)₃OH | 1.86(m,2H), 2.53(s,3H), 2.62(s,3H), 3.56(m,2H), 3.84(t,2H), 4.88(s,2H), 6.14(m,1H), 6.20(m,2H), 6.76(m,1H), 7.48(s,2H), 9.22(brs,1H) |
| HO(CH)₃CH₂N(CH₂)₂OH | 1.98(m,2H), 2.44(s,3H), 2.65(s,3H), 3.67(t,2H), 3.84–4.02(m,6H), 7.48(s,2H) |
| HO(CH₂)₂N(CH₂)₂OH | 2.44(s,3H), 2.64(s,3H), 3.9–4.1(m,8H), 7.47(s,2H) |
| EtO(CH₂)₂N(CH₂)₂OEt | 1.18(t,6H), 2.44(s,3H), 2.66(s,3H), 3.51(q,4H), 3.74(t,4H), 4.09(t,4H), 7.47(s,2H) |
| EtOCO(CH₂)₂NEt | 1.26(t,3H), 1.37(t,3H), 2.47(s,3H), 2.64(s,3H), 2.80(t,2H), 3.87(q,2H), 4.01(t,2H), 4.18(q,2H), 7.50(s,2H) |
| n-BuN—(CH₂)₃OH | 1.03(t,3H), 1.4–1.6(m,2H), 1.7–2.0(m,4H), 2.47(s,3H), 2.66(s,3H), 3.5–3.65(m,2H), 3.81(dd,2H), 3.95(t,2H), 4.78(brs,1H,OH), 7.50(s,2H) |
| n-BuNMe | 0.96(t,3H), 1.38(m,2H), 1.69(m,2H), 2.45(s,3H), 2.62(s,3H), 3.36(s,3H), 3.77(t,2H), 7.47(s,2H) |
| EtN(CH₂)₂COOH | 1.41(t,3H), 2.63(s,3H), 2.64(s,3H), 2.83(t,2H), 3.80–4.00(m,4H), 7.48(s,2H) |
| n-BuN(CH₂)₄OH | 0.94(t,3H), 1.37(m,2H), 1.54–1.80(m,6H), 2.44(s,3H), 2.61(s,3H) |
| p-HO—PhCH₂N(CH₂)₃OH | 1.7–1.9(m,2H), 2.51(s,3H), 2.56(s,3H), 3.57(t,2H), 3.86(t,2H), 4.75(brs,1H), 5.08(s,2H), 5.95(brs,1H), 6.65(d,2H), 7.16(d,2H), 7.46(s,2H) |
| H₂NCO(CH₂)₂NEt | 1.32(t,3H), 2.41(s,3H), 2.59(s,3H), 2.64(t,2H), 3.83(q,2H), 3.96(t,2H), 5.10(brs,1H), 6.40(brs,1H), 7.45(s,2H) |
| EtHNCO(CH₂)₂NEt | 1.14(t,3H), 1.37(t,3H), 2.47(s,3H), 2.60(t,2H), 2.65(s,3H), 3.30(q,2H), 3.89(q,2H), 4.02(t,2H), 6.05(brs,1H), 7.50(s,2H) |
| Pr—N—Pr | 0.98(t,6H), 1.76(m,4H), 2.46(s,3H), 2.64(s,3H), 3.71(dd,4H), 7.49(s,2H) |
| cyclopropyl-CH₂N—Pr | 0.31(m,2H), 0.61(m,2H), 1.01(t,3H), 1.10–1.30(m,1H), 1.70–1.90(m,2H), 2.47(s,3H), 2.65(s,3H), 3.67(d,2H), 3.84(dd,2H), 7.49(s,2H) |
| EtCH(CH₃)CH₂N(CH₂)₂OH | 0.92(t,6H), 1.10–1.30(m,2H), 1.40–1.55(m,2H), 1.75–1.95(m,2H), 2.48(s,3H), 2.65(s,3H), 3.88(dd,2H), 3.85–3.95(m,4H), 5.50(brs,1H), 7.51(s,2H) |
| CH₃CON—Bu | 0.88(t,3H), 1.32(m,2H), 1.56(s,3H), 1.62(m,2H), 2.06(s,3H), 2.64(s,3H), 2.72(s,3H), 3.93(t,2H), 7.53(s,2H) |
| MeO(CH₂)₂N(CH₂)₂OMe | 2.46(s,3H), 2.64(s,3H), 3.39(s,6H), 3.73(t,4H), 3.12(t,4H), 7.52(s,2H) |
| cyclopropyl-CH₂—N—(CH₂)₂OH | 0.31(q,2H), 0.71(q,2H), 1.10–1.30(m,1H), 2.48(s,3H), 2.66(s,3H), 3.76(d,2H), 3.90–4.10(m,4H), 7.51(s,2H) |
| Me₂N(CH₂)₂NEt | 1.38(t,3H), 2.35(s,6H), 2.46(s,3H), 2.64(s,3H), 2.60–2.70(m,2H), 3.80–3.95(m,4H), 7.51(s,2H) |
| CH₂=CHCH₂NCH₂CH=CH₂ | 2.48(s,3H), 2.64(s,3H), 4.38(d,4H), 5.25(dd,2H), 5.30(s,1H), 5.90–6.10(m,2H), 7.50(s,2H) |
| CH≡CH₂NCH₂C≡CH | 2.32(t,2H), 2.52(s,3H), 2.65(s,3H), 4.67(d,4H), 7.48(s,2H) |

Example 3

The following compounds were prepared starting with the appropriate amine and 4-chloro-3-methylsulfanyl-1-(2,4-dichloro-6-trifluoromethylphenyl)-1H-pyrazolo[3,4-d]pyrimidine and employing the procedure of Example 1.

TABLE 2

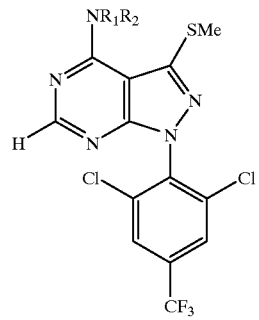

| NR₁R₂ | $^1$H NMR (CDCl$_3$) ppm |
|---|---|
| m-Me—PhCH₂NH | 2.36(s,3H), 2.65(s,3H), 4.82(d,2H), 6.20(t,1H), 7.06–7.30(m,4H), 7.73(s,2H), 8.38(s,1H) |
| pyrrolidinyl | 2.05(m,4H), 2.65(s,3H), 3.95(m,4H), 7.75(s,2H), 8.30(s,1H) |
| pyrrolyl | 2.65(s,3H), 6.50(m,2H), 7.72(m,2H), 7.80(s,2H), 8.75(s,1H) |
| thiazolidinyl | 2.66(s,3H), 3.16(t,2H), 4.25(t,2H), 7.75(s,2H), 8.35(s,1H) |
| PhCH₂NEt | 1.29(t,3H), 2.60(s,3H), 3.80(q,2H), 5.09(s,2H), 7.2–7.4(m,5H), 7.75(s,2H), 8.33(s,1H) |
| thiomorpholinyl | 2.65(s,3H), 2.85–2.95(m,4H), 4.1–4.25(m,4H), 7.75(s,2H), 8.35(s,1H) |
| PhCH₂N(CH₂)₂OH | 2.55(s,3H), 3.8–3.95(m,4H), 5.40(s,2H), 7.30–7.45(m,5H), 7.75(s,2H), 8.32(s,1H) |
| NEt₂ | 1.36(t,6H), 2.67(s,3H), 3.85(q,4H), 7.76(s,2H), 8.31(s,1H) |
| PhCH₂NMe | 2.62(s,3H), 3.35(s,3H), 5.08(s,2H), 7.3–7.4(m,5H), 7.75(s,2H), 8.35(s,1H) |
| EtN(CH₂)₂OH | 1.45(t,3H), 2.69(s,3H), 3.9–4.05(m,6H), 7.77(s,2H), 8.27(s,1H) |
| Et₂N(CH₂)₂N(CH₂)₂OH | 1.03(t,6H), 2.58(q,4H), 2.66(s,3H), 2.9–3.0(m,2H), 3.9–4.2(m,6H), 7.76(s,2H), 8.31(s,1H) |
| HO(CH₂)₂N(CH₂)₂OH | 2.68(s,3H), 3.95–4.15(m,8H), 7.77(s,2H), 8.27(s,1H) |
| n-BuN(CH₂)₂OH | 0.98(t,3H), 1.37–1.52(m,2H), 1.7–1.9(m,2H), 2.68(s,3H), 3.8–4.0(m,2H), 3.91(s,4H), 7.77(s,2H), 8.28(s,1H) |
| p-Cl—PhCH₂N(CH₂)₂OH | 2.60(s,3H), 3.90(s,4H), 5.19(s,2H), 7.25–7.45(m,4H), 7.78(s,2H), 8.35(s,1H) |
| PhCH₂N(CH₂)₃OH | 1.8–1.9(m,2H), 2.58(s,3H), 3.61(t,2H), 3.89(t,2H), 5.19(s,2H), 7.25–7.50(m,5H), 7.78(s,2H), 8.36(s,1H) |
| p-Cl—PhCH₂NH | 2.71(s,3H), 4.87(d,2H), 6.27(t,1H), 7.37(s,4H), 7.77(s,2H), 8.42(s,1H) |
| p-Cl—PhCH₂N(CH₂)₂CH₃ | 0.95(t,3H), 1.65–1.85(m,2H), 2.65(m,3H), 3.69(dd,2H), 5.06(s,2H), 7.2–7.4(m,4H), 7.77(s,2H), 8.35(s,1H) |
| p-Cl—PhCH₂N(CH₂)₃CH₃ | 0.93(t,3H), 1.20–1.45(m,4H), 1.6–1.8(m,2H), 2.64(s,3H), 3.72(dd,2H), 5.06(s,2H), 7.2–7.4(m,4H), 7.77(s,2H), 8.35(s,1H) |
| m-Cl—PhCH₂N(CH₂)₃OH | 1.8–1.95(m,2H), 2.57(s,3H), 3.60(m,2H), 3.9(t,2H), 5.12(s,2H), 7.15–7.35(m,4H), 7.75(s,2H), 8.35(s,1H) |

TABLE 3

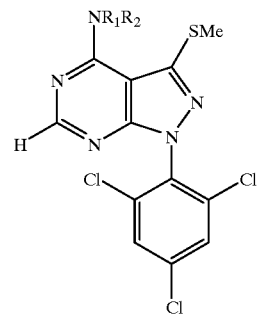

| NR₁R₂ | $^1$H NMR (CDCl$_3$) ppm |
|---|---|
| PhCH₂N(CH₂)₂OH | 2.59(s,3H), 3.7–4.0(m,4H), 5.23(s,2H), 7.3–7.45(m,5H), 7.53(s,2H), 8.34(s,1H) |
| PhCH₂N(CH₂)₃OH | 1.75–1.90(m,2H), 2.57(s,3H), 3.57(t,2H), 3.87(t,2H), 5.18(s,2H), 7.25–7.45(m,5H), 7.52(s,2H), 8.34(s,1H) |
| p-Cl—PhCH₂N(CH₂)₂OH | 2.57(s,3H), 3.86(s,4H), 4.35(brs,1H), 5.16(s,2H), 7.2–7.4(m,4H), 7.51(s,2H), 8.32(s,1H) |
| p-Cl—PhCH₂N(CH₂)₃OH | 1.72–1.88(m,2H), 2.52(m,3H), 3.54(t,2H), 3.80(t,2H), 5.05(s,2H), 7.1–7.35(m,4H), 7.45(s,2H), 8.25(s,1H) |

Example 5

The following compounds were prepared starting with the appropriate amine and the appropriate 4-chloro-1H-pyrazolo [3,4-d]pyrimidine and employing the procedure of Example 1.

3-{benzyl-[6-ethyl-3-methylsulfanyl-1-(2,4,6-trichlorophenyl)-1H-pyrazolo[3,4-d]pyrimidin-4-yl]-amino}-propanol:

$^1$H NMR (CDCl$_3$): 1.25(t,3H), 1.82(m,2H), 2.52(s,3H), 2.76(q,2H), 3.58(t,2H), 3.87(t,2H), 5.15(s,2H), 7.25–7.4(m, 5H), 7.50(s,2H)ppm.

3-{(p-chlorobenzyl)-[6-methyl-3-methylsulfanyl-1-(2,6-dichloro-4-trifluoromethylphenyl)-1H-pyrazolo [3,4-d]pyrimidin-4-yl]-amino}-propanol:

$^1$H NMR (CDCl$_3$): 1.83(m,2H), 2.52(s,3H), 2.55(s,3H), 3.59(m,2H), 3.88(t,2H), 4.36(t,1H), 5.12(s,2H), 7.2–7.4(m, 4H), 7.76(s,2H)ppm.

3-{benzyl-[6-methyl-3-methylsulfanyl-1-(2,6-dichloro-4-trifluoromethylphenyl)-1H-pyrazolo[3,4-d]pyrimidin-4-yl]-amino}-propanol:

$^1$H NMR (CDCl$_3$): 1.80(m,2H), 2.50(s,3H), 2.52(s,3H), 3.55(t,2H), 3.88(t,2H), 5.15(s,2H), 7.25–7.45(m,5H), 7.75 (s,2H)ppm.

3-{benzyl-[6-methyl-3-methylsulfanyl-1-(2,4,6-trimethylphenyl)-1H-pyrazolo[3,4-d]pyrimidin-4-yl]-amino}-propanol:

$^1$H NMR (CDCl$_3$): 1.75–1.85(m,2H), 1.95(s,6H), 2.33(s, 3H), 2.50(s,6H), 3.51(t,2H), 3.90(t,2H), 5.20(s,2H), 7.0(s, 2H), 7.25–7.45(m,5H)ppm.

3-{benzyl-[3,6-dimethyl-1-(2,4,6-trichlorophenyl)-1H-pyrazolo[3,4-d]pyrimidin-4-yl]-amino}-propanol:

$^1$H NMR (CDCl$_3$): 1.84–2.0(m,2H), 2.41(s,3H), 2.51(s, 3H), 3.55(t,2H), 3.91(t,2H), 4.99(s,2H), 7.3–7.5(m,5H), 7.47(s,2H)ppm.

Example 4

The following compounds were prepared starting with the appropriate amine and 4-chloro-3-methylsulfanyl-1-(2,4,6-trichlorophenyl)-1H-pyrazolo[3,4-d]pyrimidine and employing the procedure of Example 1.

3-{(4-methylbenzyl)-[6-methyl-3-propyl-1-(2,4,6-trichlorophenyl)-1H-pyrazolo[3,4-d]pyrimidin-4-yl]-amino}-propanol:

$^1$H NMR (CDCl$_3$): 0.78(t,3H), 1.65–1.90(m,4H), 2.38(s,3H), 2.54(s,3H), 2.77(t,2H), 3.57(t,2H), 3.89(t,2H), 4.93(s,2H), 7.18(q,4H), 7.50(s,2H)ppm.

3-{(4-methylbenzyl)-[6-methyl-1-(2,4,6-trichlorophenyl)-1H-pyrazolo[3,4-d]pyrimidin-4-yl]-amino}-propanol:

$^1$H NMR (CDCl$_3$): 1.85(m,2H), 2.32(s,3H), 2.52(s,3H), 3.57(m,2H), 3.96(t,2H), 4.92(s,2H), 5.51(brs, 1H), 7.1–7.2 (m,4H), 7.50(s,2H)ppm.

3-{(4-methylbenzyl)-[6-methyl-3-ethyl-1-(2,4,6-trichlorophenyl)-1H-pyrazolo[3,4-d]pyrimidin-4-yl]-amino}-propanol:

$^1$H NMR (CDCl$_3$): 1.23(t,3H), 1.78(m,2H), 2.34(s,3H), 2.50(s,3H), 3.54(t,2H), 3.85(t,2H), 4.90(s,2H), 7.15(q ,4H), 7.48(s,2H)ppm.

3-{(4-methylbenzyl)-[3,6-dimethyl-1-(2,4,6-trimethylphenyl)-1H-pyrazolo[3,4-d]pyrimidin-4-yl]-amino}-propanol:

$^1$H NMR (CDCl$_3$): 1.82(m,2H), 1.90(s,6H), 2.3(s,3H), 2.35(s,3H), 2.41(s,3H), 2.55(s,3H), 3.55(t,2H), 3.93(t,2H), 4.95(s,2H), 6.94(s,2H), 7.18(q,4H)ppm.

3-{benzyl-[6-chloro-3-methylsulfanyl-1-(2,4,6-trichlorophenyl)-1H-pyrazolo[3.4-d]pyrimidin-4-yl]-amino}-propanol:

$^1$H NMR (CDCl$_3$): 1.85(m,2H), 2.54(s,3H), 3.62(t,2H), 3.85(t,2H), 5.17(s,2H), 7.25–7.4(m,5H, 7.50(s,2H)ppm.

3-{benzyl-[3methylsulfanyl-6-trifluoromethyl-1-(2,4,6-trichlorophenyl)-1H-pyrazolo[3,4-d]pyrimidin-4-yl]-amino}-propanol:

$^1$H NMR (CDCl); 1.96(m,2H), 2.11(t,1H), 2.60(s,3H), 3.68(q,2H), 3.93(t,2H), 5.22(s,2H), 7.27–7.4(m,5H 7.55(s,2H)ppm.

3-{benzyl-[3-methylsulfanyl-1-(α-naphthyl)-1H-pyrazolo[3,4-d]pyrimidin-4-yl]-amino}-propanol:

$^1$H NMR (CDCl$_3$): 2.60(s,3H), 3.8–4.0(m,4H), 5.25(s,2H), 7.25–7.70(m,10H), 7.9–8.05(m,2H), 8.30(s,1H) ppm.

2-{butyl-[6-methyl-3-methylsulfanyl-1-(2,4-dichloro-6-trifluoromethylphenyl)-1-H-pyrazolo[3,4-d]pyrimidin-4-yl]-amino}-ethanol:

$^1$H NMR (CDCl$_3$): 1.0(t,3H), 1.45(m,2H), 1.77(m,2H), 3.84–4.)(m,6H), 5.62(brs,1H), 7.72(s,2H)ppm.

ethyl-butyl-[6-chloro-3-methylsulfanyl-1(2,4,6-trichlorophenyl)-1H-pyrazolo[3,4-d]pyrimidin-4-yl]-amine:

$^1$H NMR (CDCl$_3$): 0.97(t,3H), 1.34(t,3H), 1.44(m,2H), 1.72(m,2H), 2.63(s,3H), 3.73(dd,2H), 3.83(q,2H), 7.47(s,2H)ppm.

butyl-[3,6-dimethyl-1-(2,4,6-trimethylphenyl)-1H-pyrazolo[3,4-d]pyrimidin-4-yl]-ethyl-amine $^1$H NMR(CDCl$_3$):0.96(t,3H), 1.29(t,3H), 1.3–1.45(m,2H), 1.6–1.8(m,2H), 1.90(s,6H), 2.29(s,3H), 2.42(s,3H), 2.66(s,3H), 3.70(dd,2H), 3.77(q,2H), 6.92(s,2H) ppm.

sec-butyl-[3,6-dimethyl-1-(2,4,6-trimethylphenyl)-1H-pyrazolo[pyrazolo[3.4.-d]pyrimidin-4-yl]amine $^1$H NMR (CDCl$_3$):1.00(t,3H), 1.3(d,3H), 1.6–1.72(m,2H), 1.90(2 sets of s,6H), 2.30(s,3H), 2.49(s,3H, 2.62(s,3H), 4.4–4.5(m,1H), 4.9(d,1H), 6.9(s,2H) ppm.

[3,6-dimethyl-1-(2,4,6-trimethylphenyl)-1H-pyrazolo[3,4,-d]pyrimidin-4-yl](1-ethyl-propyl)-amine hydrochloride $^1$H NMR (CDCl$_3$):1.08(t,6H), 1.83(m,4h), 1.90(s,6H), 2.35(s,3H), 2.60(s,3H), 2.75(s,3H), 4.0–4.15(m,1H), 6.97(s,2H), 10.1(d,1H), 14.9(s,1H) ppm.

2-[3,6-dimethyl-1-(2,4,6-trimethylphenyl)-1H-pyrazolo[3,4,-]pyrimidin-4-ylamino]-butan-1-ol hydrochloride $^1$H NMR (CDCl$_3$):1.07(t,3H), 1.8–2.0(m,2H), 1.89(s,3H), 1.91(s,3H), 2.33(s,3H), 2.76(s,3H), 2.84(s,3H), 3.69(brs,1H), 4.03(brs,1H), 5.05(brs,1H), 6.58(brs,1H), 6.98(s,2H).

Example 6

3-{Benzyl-[6-methyl-3-methylsulfanyl-1-(2,4,6-trichlorophenyl)-1H-pyrazolo[3.4-d]pyrimidin-4-yl]-amino}-propan-1-ol acetate.

A solution of 3-{benzyl-[6-methyl-3-methylsulfanyl-1-(2,4,6-trichlorophenyl)-1H-pyrazolo[3,4-d]pyrimidin-4-yl]amino}-propanol (80 mg, 0.148 mmol) in 1 ml of methylene chloride was treated with acetic anhydrous (38 mg, 0.37 mmol) and triethyl amine (38 mg, 0.37 mmol) and stirred at room temperature for 15 hours. The mixture was quenched with water and a few drops of dilute HCl and extracted with ethyl acetate. The organic layer was neutralized with aqueous sodium bicarbonate and washed with brine, separated, dried and concentrated to give the title compound as an oil. The oil was purified through silica gel column chromatography using chloroform as eluent to give 57 mg of the title compound as a white glass form. $^1$H NMR (CDCl$_3$): 2.0(s, 3H, 2.03(m,2H), 2.45(s,3H), 2.60(s,3H), 3.74(t,2H), 4.10(t, 2H), 5.1(s,2H), 7.2–7.4(m,5H), 7.50(s,2H) ppm.

Example 7

The following compounds were prepared by the acylation of the Example 6 starting from the corresponding hydroxy derivative.

3-{(4-methyl-benzyl-[6-methyl-3-methylsulfanyl-1-(2,4,6-trichlorophenyl)-1H-pyrazolo[3.4-d]pyrimidin-4-yl]-amino}-propan-1-ol acetate:

$^1$H NMR (CDCl$_3$): 1.99(s,3H), 1.95–2.06(m,2H), 2.22(s,3H), 2.49(s,3H), 2.59(s,3H), 3.75(t,2H), 4.12(t,2H), 5.05(s,2H), 7.18(q,4H), 7.50(s,2H) ppm.

2-{ethyl-[3-methylsulfanyl-1-(2,6-dichloro-4-trifluoromethylphenyl)-1H-pyrazolo[3,4-d]pyrimidin-4-yl]-amino}-ethan-1-ol acetate:

$^1$H NMR (CDCl$_3$): 1.39(t,3H), 2.07(s,3H), 2.69(s,3H), 3.98(q,2H), 4.04(t,2H), 4.43(t,2H), 7.77(s,2H), 8.23(s,1H) ppm.

2-{butyl-[6-methyl-3-methylsulfanyl-1-(2,4,6-trichlorophenyl)-1H-pyrazolo[3,4-d]pyrimidin-4-yl]-amino}-ethan-1-ol acetate:

$^1$H NMR (CDCl$_3$): 0.98(t,3H), 1.3–1.5(m,2H), 1.65–1.85 (m,2H), 2.04(s,3H), 2.47(s,3H), 2.65(s,3H), 3.83(t,2H), 4.02 (t,2H), 4.40(t,2H), 7.50(s,2H)ppm.

Example 8

4-{N-(4-methyl-benzyl)-N-(3methoxy) propyl}amino-[6-methyl-3-methylsulfanyl-1-(2,4,6-trichlorophenyl)-1H-pyrazolo[3,4-d]pyrimidine.

A solution of 3-{(4-pyrazolo[3,4-d]pyrimidin-4-yl]-amino}-propanol (96 mg, 0.15 mmol) in 1 ml of dry tetrahydrofuran (THF) was treated with sodium hydride (60% in oil) (7 mg, 0.18 mmol), then methyl iodide was added. The mixture was stirred at room temperature for 15 hours, then quenched with water and extracted with ethyl acetate. The organic layer was dried and concentrated to give a colorless form which was purified through silica gel column chromatography using chloroform as eluent to give 60 mg of the title compound as a white glass form. $^1$H NMR (CDCl$_3$): 1.95(m,2H), 2.32(s,3H), 2.47(s,3H), 2.56(s,3H), 3.24(s,3H), 3.39(t,2H), 3.75(t,2H), 5.01(s,2H), 7.15(q,4H), 7.47(s,2H)ppm.

Example 9

The following compounds were prepared according to the procedure of the Example 8 starting with the corresponding hydroxy derivative, and alkyl iodide.

4-[benzyl-(3-ethoxypropyl)]amino-3-methylsulfanyl-6-methyl-1-(2,4,6-trichlorophenyl)-1H-pyrazolo[3,4-d]pyrimidine:

$^1$H NMR (CDCl$_3$): 1.12(t,3H), 1.97(m,2H), 2.47(s,3H), 2.56(s,3H), 3.37(q,2H), 3.48(t,2H), 3.80(t,2H), 5.07(s,2H), 7.23–7.40(m,5H), 7.49(s,2H)ppm.

4-[benzyl-(3-methoxypropyl)]amino-3-methylsulfanyl-6-methyl-1-(2,4,6-trichlorophenyl)-1H-pyrazolo[3,4-d]pyrimidine:

$^1$H NMR (CDCl$_3$): 2.0(m,2H), 2.5(s,3H), 2.57(s,3H), 3.25(s,3H), 3.4(t,2H), 3.8(t,2H), 5.1(s,2H), 7.2–7.4(m,5H), 7.48(s,2H)ppm.

Example 10

3-{Benzyl-[6-methyl-3-methylsulfanyl-1-(2,4,6-trichlorophenyl)-1H-pyrazolo[3.4-d]pyrimidin-4-yl]-amino}-propan-1-ol methylcarbamate.

A solution of 3-{benzyl-[6-methyl-3-methylsulfanyl-1-(2,4,6-trichlorophenyl)-1H-pyrazolo[3,4-d]pyrimidin-4-yl]amino}-propan-1-ol (100 mg, 0.191 mmol) in 2 ml of dry THF was treated with 6 mg of 60% sodium hydride in oil and methyl isocyanate (39 mg, 6.78 mmol) at room temperature and stirred at room temperature for 10 hours. The mixture was quenched with water and extracted with ethyl acetate. The organic layer was dried and concentrated to give 110 mg of white form. The form was purified through silica gel column chromatography to give 79 mg of the title compound as a white glass form. $^1$H NMR (CDCl$_3$): 2.03 (m,2H), 2.51(s,3H), 2.59(s,3H), 2.77(d,3H), 3.79(t,2H), 4.12(t,2H), 4.50(brs,1H), 5.17(s,2H), 7.2–7.45(m,5H), 7.51 (s,2H)ppm.

Example 11

The following compounds were prepared according to the procedure of the Example 10 starting from the corresponding hydroxy derivative and methyl isocyanate or methyl thioisocyanate.

3-{(4-methyl-benzyl)-[6-methyl-3-methylsulfanyl-1-(2,4,6-trichlorophenyl)-1H-pyrazolo[3,4-d] pyrimidin-4-yl]amino}-propan-1-ol methylcarbamate:

$^1$H NMR (CDCl$_3$): 2.02(m,2H), 2.36(s,3H), 2.49(s,3H), 2.59(s,3H), 2.77(d,3H), 3.76(t,2H), 4.12(t,2H), 4.55(brs, 1H), 5.12(s,2H), 7.29(q,4H), 7.50(s,2H)ppm.

4-[(p-methylbenzyl)-3-(N-methylsulfanylcarbamoyloxypropyl)]amino-3-methylsulfanyl-6-methyl-1-(2,4,6-trichlorophenyl)-1H-pyrazolo[3,4-]pyrimidine-4-](p-methylbenzyl)-3-(N-methylcarbamoylthiopropyl)]amino-3-methylsulfanyl-6-methyl-1-(2,4,6-trichlorophenyl)-1H-pyrazolo[3,4-d]pyrimidine:

A mixture of the title compounds was obtained in a 2:1 ratio. $^1$H NMR (CDCl$_3$): 2.05–2.25(m,2H), 2.36(s,3H), 2.52 (s,3H), 2.59(s,⅓×3H), 2.60(⅔×3H), 2.75(d, ⅓×3H), 3.05(d, ⅔×3H), 3.78(t,2H), 4.47(t,⅔×2H), 4.54(t,⅓×2H), 5.06(s, 2H), 6.2(brs,⅔H), 6.5(brs, ⅓H), 7.19(q,4H), 7.51(s,3H) ppm.

Example 12

3-{Benzyl-[6-methyl-3-methylsulfinyl-1-(2,4,6-trichlorophenyl)-1H-pyrazolo[3,4-d]pyrimidin-4-yl]-amino}-propanol.

A solution of 3-{benzyl-[6-methyl-3-methylsulfanyl-1-(2,4,6-trichlorophenyl)-1H-pyrazolo[3,4-d]pyrimidin-4-yl]-amino}propanol (42 mg, 0.077 mmol) and m-chloroperbenzoic acid (14 mg, 0.081 mmol) in 0.5 ml of methylene chloride was stirred at room temperature for 3 hours. The mixture was quenched with water and saturated sodium thiosulfate, and extracted with methylene chloride. The organic layer was washed with saturated sodium bicarbonate, dried and concentrated to give an oil which was purified through silica gel column chromatography using 2% methanol in chloroform as eluent to give 46 mg of the title compound as a white glass form. $^1$H NMR (CDCl$_3$): 1.88 (m,2H), 2.54(s,3H), 2.73(s,3H), 3.5–3.7(m,4H), 4.3(m,1H), 5.15(ABq,J$_{AB}$=16Hz,2H), 7.2–7.4(m,5H), 8.47(ABq,2H) ppm.

Example 13

The following compounds were prepared by the method of Example 12 starting with the corresponding methylsulfanyl derivative.

4-(n-butyl-ethyl)amino-3-methylsulfinyl-6-methyl-1-(2,4,6-trichlorophenyl)-1H-pyrazolo[3,4-d]pyrimidine:

$^1$H NMR (CDCl$_3$): 0.98(t,3H), 1.35(t,3H), 1.46(m,2H), 1.71(m,2H), 2.48(s,3H), 3.08(s,3H(s,3H), 3.65–4.10(m,4H), 7.52(ABq,J$_{AB}$=2 Hz,2H)ppm.

4-diethylamino-3-methylsulfinyl-6-methyl-1-(2,4,6-trichlorophenyl)-1H-pyrazolo[3,4-d]pyrimidine:

$^1$H NMR (CDCl$_3$): 1.36(t,6H), 2.49(s,3H), 3.11(s,3H), 3.78(m,2H), 3.99(m,2H), 7.52(ABq, J$_{AB}$=1.72 Hz, 2H)ppm.

Example 14

The following compounds were prepared by the method similar to that of the Example 12 starting with the corresponding methylsulfanyl derivative and 2.5 equivalents of m-chloroperbenzoic acid in methylene chloride and stirred at room temperature for 15 Hours.

3-{benzyl-[6-methyl-3-methylsulfonyl-1-(2,4,6-trichlorophenyl)-1H-pyrazolo[3,4-d]pyrimidin-4-yl]-amino}-propanol:

$^1$H NMR (CDCl$_3$): 1.8(m,2H), 2.52(s,3H), 3.40(s,3H), 3.60(t,2H), 3.90(t,2H) 5.16(s,2H), 7.2–7.4(m,4H), 7.50(s, 2H)ppm.

3-{(4-methyl-benzyl)-[6-methyl-3-methylsulfonyl-1-(2,4,6-trichlorophenyl)-1H-pyrazolo[3,4-d]pyrimidin-4-yl]-amino}-propanol:

$^1$H NMR (CDCl$_3$): 1.8(m,2H, 2.34(s,3H), 2.52(s,3H), 3.43(s,3H), 3.61(t,2H), 3.90(t,2H), 5.14(s,2H), 7.13(s,4H), 7.56(s,2H)ppm.

4-(N-butyl-N-ethyl)amino-6-methyl-3-methylsulfonyl-1-(2,4,6-trichlorophenyl)-1H-pyrazolo[3,4-d]pyrimidine:

$^1$H NMR (CDCl$_3$): 0.95(t,3H), 1.30(t,3H), 1.37(m,2H), 1.69(m,2H), 2.47(s,3H), 3.42(s,3H), 3.85(t,2H), 3.93(q,2H), 7.53(s,2H)ppm.

4-N,N-diethylamino-6-methyl-3-methylsulfonyl-1-(2,4,6-trichlorophenyl)-1H-pyrazolo[3,4-d] pyrimidine:

$^1$H NMR (CDCl$_3$): 1.29(t,3H, 2.45(s,3H), 3.40(s,3H), 3.91(q,2H), 7.50(s,1H)ppm.

2-{N-butyl-N-[6-methyl-3-methylsulfonyl-1-(2,4,6-trichlorophenyl)-1H-pyrazolo[3,4-d]pyrimidin-4-yl]-amino}-ethanol:

$^1$H NMR (CDCl$_3$): 0.95(t,3H), 1.30–1.50(m,2H), 1.50–1.70(m,2H), 2.66(s,3H), 2.76(t,2H), 3.16(t,2H), 3.44(s,3H), 3.9–4.0(m,1H), 4.79(t,2H), 7.55(s,2H)ppm.

Example 15

Ethyl-butyl-[6-methoxy-3-methylsulfanyl-1-(2,4,6-trichlorophenyl)-1H-pyrazolo[3,4-d]pyrimidin-4-yl] amine To 1 ml of methanol was added sodium (25 mg) and the mixture was stirred until all the sodium was dissolved completely. The resulting solution was treated with ethyl-butyl-[6-chloro-3-methylsulfanyl-1-(2,4,6trichlorophenyl)-1H-pyrazolo[3,4-d]pyrimidine-4-yl]amine (100 mg, 0.21 mmol) and heated at reflux for 3 hours. The mixture was quenched with water and extracted with ethyl acetate. The organic layer was dried and concentrated to give an oil residue. The oil residue was purified by silica gel column chromatography to give 73 mg of the title compound as a colorless oil. $^1$H NMR (CDCl$_3$):0.96(t,3H), 1.35(t,3H), 1.42 (m,2H), 1.71(m,2H), 2.63(s,3H), 3.74(dd,2H), 3.86(q,2H), 3.91(s,3H), 7.46(s,2H)ppm.

Example 16

2-Butyl-2-[6-methyl-3-methylsulfanyl-1-(2,4,6-trichlorophenyl)-1H-pyrazolo[3,4-d]pyrimidin-4-yl]-malonic acid dimethylester A suspension of 60% sodium hydride in oil (0.240 g, 6 mmol) in 5 ml of dimethylsulfoxide (DMSO) was treated with dimethyl butylmalonate (0.948 g, 6 mmol). After stirring for 10 minutes, 4-chloro-3-thiomethyl-6-methyl-1-(2,4,6-trichlorophenyl-1H-pyrazolo[3,4-d]pyrimidine (1.182 g, 3 mmol) was added and the resulting mixture was heated at 100° C. for 1 hour. The mixture was quenched with water and extracted with ethyl acetate. The organic layer was dried and concentrated to give the crude product as an oil which was diluted with 2-propanol and concentrated to dryness to give a yellow solid. The solid was purified through silica gel column chromatography, using 60:40 of chloroform: hexane to 80:20 of chloroform: hexane as eluent, to give 1.349 g of product as a yellow solid which was triturated with methanol to give 669 mg of yellow solid, m.p. 146–152° C.; $^1$H NMR(CDCl$_3$): 0.81(t,3H), 1.10–1.40 (m,4H), 2.54–2.63(m,2H), 2.65(s,3H), 2.66(s,3H), 3.84(s, 6H), 7.52(s,2H)ppm.

Example 17

2-Butyl-2-[6-methyl-3-methylsulfanyl-1-(2,4,6-trichlorophenyl)-1H-pyrazolo[3,4-d]pyrimidin-4-yl]-malonic acid diethylester The title compound was prepared starting with diethyl butylmalonate and employing the procedure of Example 16, m.p. 148–150° C.; $^1$H NMR(CDCl$_3$): 0.80(t,3H), 1.1–1.4 (m,10H), 2.45–2.65(m,2H), 2.63(s,3H), 2.64(s,3H), 4.29(q, 4H), 7.50(s,2H)ppm.

Example 18

2-[6-Methyl-3-methylsulfanyl-1-(2,4,6-trichlorophenyl)-1H-pyrazolo[3,4-d]pyrimidin-4-yl] hexanonic acid methyl ester A solution of 2-butyl-2-[6-methyl-3-methylsulfanyl-1-(2, 4,6-trichlorophenyl)-1H-pyrazolo[3,4-d]pyrimidin-4-yl]-malonic acid dimethylester (311 mg, 0.57 mmol) in 4 ml of toluene was treated with 1.5 M diisobutylaluminum hydride (DIBAL) (0.84 ml, 1.254 mmol)and stirred at room temperature for 1 hour. An additional 0.3 ml of DIBAL was added and the resulting mixture was stirred for an additional 15 minutes. The mixture was quenched with methanol and stirred for 1 hour and filtered through celite. The filtrate was concentrated to dryness. The residue was taken up with water and chloroform. The organic layer was dried and concentrated to give 290 mg of crude material which was purified through silica gel, using chloroform as eluent, to give 164 mg of the title compound as a yellow solid. $^1$H-NMR(CDCl$_3$): 0.87(t,3H), 1.2–1.5(m,4H), 1.96–2.10(m, 1H), 2.1–2.3(m,1H), 2.68(s,3H), 2.69(s,3H), 3.71(s,3H), 4.22(t,1H), 7.50(s,2H)ppm.

Example 19

2-[6-Methyl-3-methylsulfanyl-1-(2,4,6-trichlorophenyl)-1H-pyrazolo[3,4-d]pyrimidin-4-yl-hexanonic acid ethyl ester The title compound was prepared by the method of Example 18 starting with 2-butyl-2-[6-methyl-3-methylsulfanyl-1-1-(2,4,6-trichlorophenyl)-1H-pyrazolo[3, 4-d]pyrimidin-4-yl]-malonic acid diethylester. $^1$H NMR (CDCl$_3$): 0.88(t,3H), 1.20(t,3H), 1.2–1.5(m,4H), 2.0–2.1(m, 1H), 2.1–2.3(m,1H), 2.67(s,3H), 2.69(s,3H), 4.19(q, 2H), 4.39(t,1H), 7.50(s,2H)ppm.

Example 20

2-Ethyl-2-[6-methyl-3-methylsulfanyl-1-(2,4,6-trichlorophenyl)-1H-pyrazolo[3,4-s]pyrimidin-4-yl]-hexanonic aced methyl ester A solution of 2-[6-methyl-3-methylsulfanyl-1-(2,4,6-trichlorophenyl)-1H-pyrazolo[3,4-d]pyrimidin-4-yl]-hexanonic acid methyl ester (217 mg, 0.44 mmol) in 1 ml of DMSO was treated with 60% sodium hydride in oil (46 mg, 1.15 mmol). After stirring for 20 minutes at room temperature, ethyl iodide (0.2 ml) was added and the mixture was stirred at room temperature for 15 hours. The mixture was quenched with brine and extracted with ethyl acetate. The organic layer was washed twice with brine, separated, dried and concentrated to give 233 mg of the crude material which was purified through silica gel column chromatography, using methylene chloride as eluent, to give 146 mg of the title compound as an off-white solid. $^1$H NMR(CDCl$_3$): 0.74(t,3H), 0.83(t,3H), 1.2–1.4(m,2H), 2.1–2.55(m,4H), 2.64(s,3H), 2.70(s,3H, 3.74(s,3H), 7.51(s, 2H)ppm.

Example 21

4-(1-Ethyl-phenyl)-6-methyl-3-methylsulfanyl-1-(2, 4,6-trichlorophenyl)-1H-pyrazolo[3,4-d]pyrimidine and 3-[6-methylsulfanyl-1-(2,4,6-trichlorophenyl)-1H-pyrazolo[3,4-d]pyrimidin-4-yl]-heptan-3-ol A solution of 2-methyl-2-[6-methyl-3-methylsulfanyl-1-(2,4,6-trichlorophenyl)-1 H-pyrazolo[3,4-d]pyrimidin-4-yl]-hexanonic acid methyl ester (89 mg, 0.173 mmol) in 2 ml of dimethylformamid (DMF) was treated with lithium iodide and heated at reflux for 5 hours. An additional lithium iodide (433 mg) was added and the mixture was heated for an additional 1 hour. The mixture was neutralized with acid and extracted with ethyl acetate. The organic layer was washed with brine, dried and concentrated to give 79 mg of the crude material which contains two major components which were separated by column chromatography to give two fractions. One of the fractions showed a pure component of 3-[6-methyl-3-methylsulfanyl-1-(2,4,6-trichlorophenyl)-1H-pyrazolo[3,4-d]pyrimidin-4-yl]-heptan-3-ol and the other reaction contained a mixture of the title compounds a weight ration of 55 to 45. $^1$H NMR(CDCl$_3$) for 3-[6-methyl-3-methylsulfanyl-1-(2,4,6-trichlorophenyl)-1H-pyrazolo[3,4-d]pyrimidin-4-yl]-heptan-3-ol: 0.68(t,3H), 0.79(t,3H), 0.8 (m,1H), 1.1–1.5(m,3H), 2.0–2.2(m,2H), 2.2–2.5(m,2H), 2.67(s,3H), 2.72(s,3H), 5.79(s,1H), 7.51(s,2H)ppm. 1H NMR (CDCl$_3$), for the mixture of the title compounds: 1.42–2.4(m,1OH), 1.6–1.8(m,0.55×2H), 1.8–2.0(m,0.55× 2H), 2.0–2.2 (m,0.45×2H), 2.2–2.4(m,0.45×2H), 2.665(s, 0.55×3H), 2.672(s,0.45×3H), 2.686(s,0.55×3H), 2.718 (0.45×2H), 3.34(m,0.55H), 5.79(s,0.45H), 7.49(s,0.55×2H), 7.51 (s,0.45×2H)ppm.

Example 22

A. 2-(2-Ethyl-butyryl)-3-ethoxy-but-2-enenitrile

A mixture of 4-ethyl-3-oxo-hexanenitrile (1.013 g, 7.28 mmol), acetic anhydride (1.5 ml) and triethyl orthoacetate (1.240 g, 7.64 mmol) was heated to reflux overnight. The reaction mixture was taken up in ethyl acetate and water. The brine and the ethyl acetate layer were separated. The organic layer was dried and concentrated to give 1.262 g of dry oil which was used directly for the next reaction. $^1$H NMR (CDCl$_3$): 0.8–1.0(m,6H), 1.44(t,3H), 1.4–1.8(m,4H), 2.61(s, 3H), 3.03(m,1H), 4.28(q, 2H)ppm.

B. 1-[5-amino-3-methyl-1-(2,4,6-trimethylphenyl)-1H-pyrazol-4-yl]-2-ethyl-butan-1-one A mixture of 2-(2-ethyl-butyl)-3-ethoxy-but-2-enenitrile (407 mg 1.94 mmol) and trimethylphenylhydrazine (280 mg, 1.86 mmol) in 5 ml of methanol was heated at reflux for 5 hours. The mixture was quenched with water and extracted with ethyl acetate. The organic layer was dried and concentrated to give 584 mg of brown oil. The brown oil was purified through silica gel column chromatography, using 1:1 of hexane: chloroform as eluent, to give 222 mg of yellow solid. 1H NMR (CDCl3): 0.8–1.0(two sets of t,6H), 1.4–1.9(m,4H), 2.04(s,6H, 2.22(s,3H, 2.32(s,3H), 2.54(s, 3H), 2.85–3.05(m,1H), 5.71(brs,2H), 6.97(s,2H)ppm.

C. 4-(1-ethyl-propyl)-6-methyl-3-methylsulfanyl-1-(2,4,6-trimethylphenyl)-1H-pyrazolo[3,4-d]pyrimidine A mixture of 1-[5-amino-3-methyl-1-(2,4,6-trimethylphenyl)-1H-pyrazol-4-yl]2-ethyl-butan-1-one (598 mg, 1.91 mmol), acetamide (2.311 g, 39.1 mmol) and ammonium chloride (2.057 g, 38.5 mmol) was heated at reflux of 5 hours. An additional 2.029 g of acetamide was added and the mixture was heated for an additional 16 hours (tlc showed some starting material left). An additional 2.049 g of acetamide was added and the mixture was heated an additional 6 hours and GC-MS showed that the reaction was finished. The mixture was quenched with water and extracted with ethyl acetate. The organic layer was dried and concentrated to dryness to give a brown oil. The brown oil was purified through silica gel column chromatograph to give 221 mg of the title compound as an oil. 1H NMR (CDCl3): 0.86(t,6H), 1.70–1.85(m,2H), 1.91(s,6H), 1.90–2.05(m,2H), 2,34(s,3H), 2.70(s,3H), 2.74(s,3H) 3.15–3.30(m,1H), 6.98(s,2H)ppm.

Example 23

4-(1-methoxymethyl-propoxy)-3,6-dimethyl-1-(2,4, 6-trimethylphenyl)-1H-pyrazolo[3,4-d]pyrimidine A mixture of 1-methoxy-2 butanol (208 mg, 1.99 mmol) and sodium hydride (53 mg, 1.33 mmol) in dry THF (1 ml) was stirred at room temperature for 10 minutes. The mixture was treated with 4-chloro-3,6-dimethyl-1-(2,4,6-trimethylphenyl)-1H-pyrazoloro[3,4d]pyrimidine (200 mg, 0.665 mmol) and stirred at room temperature for 2 hours. The mixture was quenched with water and extracted with ethyl acetate. The organic layer was dried and concentrated to give an oil which was purified through silica gel column chromatography using chloroform as eluent to give 185 mg of the title compound as an off-white solid. 1H NMR (CDCl3): 1.02 (9t,3H), 1.7–1.9(m,2H), 1.90(s,3H), 1.91(s, 3H), 2.30(s,3H), 2.53(s,3H), 2.62(s,3H), 3.41(s,3H), (3.5–3.89(m,2H), 5.64(m,1H), 6.94(s,2H) ppm.

Example 24

A. 2-(2-Ethyl-hexanoyl)-3-methoxy-but-2-enentrile

The title compound was prepared by the method of Example 22A starting with 4-ethyl-3-oxo-octanenitrile, acetic anhydride and trimethyl orthoacetate to give a brown oil which was purified through silica gel to give a light brown oil as a mixture of two isomers. $^1$H NMR (CDCl$_3$): 0.8–0.95 (m,6H), 1.1–1.8(m,8H), 2.62(2 sets of s,3H), 3.0–3.2(m, 1H), 4.0(two sets of s)ppm.

B. 1-[5-amino-3-methyl-1-(2,4,6-trimethylphenyl)-1H-pyrazol-4-yl]2-ethyl-hexan-1-one The title compound was prepared by the method of Example 22B starting with 2-(2-ethyl-hexanoyl)-3-methoxy-but-2-eneitrile and trimethylphenylhydrazine, as a yellow oil. 1H NMR (CDCl$^3$):0.85–1.0(m,6H), 1.20–1.40 (m,4H), 1.40–1.70(m,2H), 1.70–1.85(m,2H), 2.026(s,3H), 2.033(s,3H), 2.32(s,3H), 2.51(s,3H), 2.98–3.05(m,1M), 5.67 (s,2H), 6.96(s,2H)ppm.

C. 4-(1-ethyl-pentyl)-6-methyl-3-methylsulfanyl-1-(2,4,6-trimethylphenyl)-1H-pyrazolo[3,4-d] pyrimidine The title compound was prepared by the method of Example 22C starting with 1-[5-amino-3-methyl-1-(2,4,6- trimethylphenyl)-1H-pyrazol-4-yl]2-ethyl-hexan-1-one and acetamide to give the title compound as a clear oil. 1H NMR (CDCl$^3$): 0.86(t,6H), 1.2–1.4(m, 4H), 1.7–1.9(m,2H), 1.92–2.0(m,2H), 1.91(s,3H), 1.93(s,3H), 2.35(s,3H), 2.70(s, 3H),2.74(s,3H), 3.24–3.35(m,1H), 6.99(s,2H)ppm.

The following Preparations illustrate the preparation of the starting materials used in the above Examples.

Preparation A

5-Amino-3-methylsulfanyl-1-(2,4,6-trichlorophenyl)-1H-pyrazole-4-carboxamide:

A mixture of bis(methythio)methylenecyanoacetamide (7.800 g, 50 mmol) and 2,4,6-trichlorophenylhydrazine (10.575 g, 50 mmol) in 250 ml of methanol was heated at reflux for 2.5 hours. The mixture was cooled and water was added. Precipitate formed and filtered to give 14.323 g (81.5% yield) of the title compound as a white solid. $^1$H NMR(CDCl$_3$): 2.6 (s,3H), 5.5(brs, 2H), 7.5(s,2H) ppm. Recrystallization of a small portion of the solid from chloroform gave white crystals; m. p. 198–199° C. Anal. Calc. for C$_{11}$H$_9$Cl$^3$N$^4$OS: C, 37.57; H, 2.58; N, 15.93; Found: C, 37.54; H, 2.51; N, 15.73.

Preparation B 1. 5-Amino-3-methylsulfanyl-1-(2,6-dichloro-4-trifluoromethylphenyl)-1H-pyrazole-4-carboxamide The title compound was prepared as a white solid by the procedure of Preparation A starting with 2,6-dichloro-4-trifluoromethypphenylhydrazine. $^1$H NMR (CDCl$_3$): 2.58(s, 3H), 5.25(brs,2H), 7.72(s,2H)ppm.

2. 5-amino-3-methylsulfanyl-1-(2,4,6-trimethylphenyl)-1H-pyrazole-4-carboxamide.

The title compound was prepared as a white solid by the procedure of Preparation A starting from 2,4,6-trimethylphenylhydrazine. $^1$H NMR (CDCl$_3$): 1.98 (s,6H), 2.25(s,3H), 2.5(s,3H), 5.2(s,3H), 7.9(s,2H) ppm.

3. 5-amino-3-methylsulfanyl-1-(2,6-dichloro-4-trifluoromethylphenyl)-1H-pyrazole-4-carbonitrile The title compound was prepared by the procedure of Preparation A starting with bis(methylsulfanyl) methylenemalononitrile and 2,6-dichloro-4-trifluoromethylphenylhydrazinee. 1H NMR (CDCl$^3$): 2.5(s, 3H), 4.5(s,2H), 7.75(s,2H)ppm.

4. 5-amino-1-(2,4,6-trichlorophenyl)-1H-pyrazole-4-carbonitrile

The title compound was prepared as an orange solid, m.p. 208.5–209.5° C. by the procedure of Preparation A starting with ethoxymethylenemalononitrile and 2,4,6-trichlorophenylhydrazine.

$^1$H NMR (CDCl$_3$): 4.5(brs,2H), 7.5(s,2H), 7.7(s,1H)ppm.

Preparation C

5-Amino-3-methylsulfanyl-1-(2,6-dichloro-4-trifluoromethylphenyl)-1H-pyrazole-4-carboxamide.

A mixture of 5-amino-3-methylsulfanyl-1-(2,6-dichloro-4-trifluoromethylphenyl)-1H-pyrazole-4-carbonitrile (2.7 g, 7.35 mmol), 30% hydrogen peroxide (10 ml), ammonium hydroxide (90 ml), methanol (70 ml) and water (15 ml) was stirred in a pressure reactor for 10 hours. The mixture was filtered and washed with water to give an off-white solid. The filtrate was diluted with water and extracted with ethyl acetate. The organic layer was dried and concentrated to recover more product as an off-white solid. Both portions of off-white solid were combined to give 1.400 g of the desired title compound which was identical to the first title compound of Preparation B.

Preparation D

5Amino-1-(2,4,6-trichlorophenyl)-1H-pyrazole-4-carboxamide.

To a cooled concentrated sulfuric acid (10 ml) was added portionwise 5-amino-1-(2,4,6-trichlorophenyl)-1H-pyrazole-4-carbonitrile (4.000 g, 13.9 mmol) over a period of 45 minutes. The reaction mixture was allowed to stir at room temperature for 1 hour after addition. The mixture was poured over ice with stirring and the solution was neutralized with 15% NaOH in ice-bath. Precipitate formed and was filtered to give 3.57 g of yellow solid. $^1$H NMR (CDCl$_3$): 5.3(brs,2H), 5.6(brs,2H), 7.5(s,2H), 7.7(s,1H) ppm.

Preparation E

2-Cyano-3-(N'-2,4,6-trichlorophenylhydrazino)but-2-enoic acid amide.

A mixture of 2-cyano-3-ethoxy-but-2-enoic acid amide (616 mg, 4 mmol) and trichlorophenylhydrazine (730 mg, 4 mmol) in 15 ml of ethanol and 3 ml of chloroform was heated at reflux for 6 hours to give 754 mg of the title compound as a white solid, m.p. 204–206° C. $^1$H NMR (DMSO-d6): 2.35(s,3H), 6.95(brs,2H), 7.6(s,2H), 7.95(s, 1H), 11.7(s,1H)ppm.

Preparation F

2-Cyano-3-(N'-2,4,6-trichlorophenylhydrazino)pent-2-enoic acid amide.

The title compound was prepared as a yellow solid by the procedure analogous to Preparation E starting from 2-cyano-3-methoxy-pent-2-enoic acid amide. $^1$H NMR (CDCl$_3$): 1.2(t,3H), 3.0(q,2H), 4.0(s,3H), 5.5(brs,1H), 6.0(brs,1H) ppm.

Preparation G 3,6-Dimethyl-1-(2,4,6-trichlorophenyl)-1H-pyrazolo [3,4-d]pyrimidine-4-ol.

A mixture of 2-cyano-3-(N'-2,4,6-trichlorophenylhydrazino)but-2-enoic acid amide (0.620 g, 2.02 mmol) and acetamide (1 g, 16.95 mmol) was heated at reflux for 15 hours. The mixture was cooled and diluted with water and extracted with chloroform. The organic layer was separated dried and concentrated to give 0.325 g (47%) of the title compound as a brown solid. $^1$H NMR (CDCl$_3$): 2.5(s,3H), 2.7(s,3H), 7.5(s,2H) ppm.

Preparation H

3-Ethyl-6-methyl-1-(2,4,6-trichlorophenyl)-1H-pyrazolo[3,4-d]pyrimidine-4-ol.

The crude material of the title compound was prepared as a brown solid by the procedure analogous to Preparation G and was used directly for the next step without purification.

Preparation I

2-Cyano-3-(N'-2,4,6-trichlorophenylhydrazino)hex-2-enoic acid amide.

The title compound was prepared as a yellow solid by the procedure analogous to Preparation E starting from 2-cyano-3-methoxy-hex-2-enoic acid. $^1$H NMR (CDCl$_3$): 1.07(t,3H), 1.71(m,2H), 2.87(dd,2H), 6.19(s,1H), 7.29(s,2H), 11.50(s, 1H)ppm.

Preparation J

5-Amino-3-n-propyl-1-(2,4,6-trichlorophenyl)-1H-pyrazole-4-carboxamide.

A solution of 2-cyano-3-(N'-2,4,6-trichlorophenylhydrazino)-hex-2-enoic acid amide (1.920 g, 5.552 mmol) and acetamide (3.262 g, 55.20 mmol) was heated at reflux for 3 hours. The reaction mixture was cooled and treated with 20 ml of water. Precipitate formed and was filtered to give 2.024 g of a beige solid. The solid was dissolved in ethyl acetate and water. The organic layer was separated, dried and concentrated to give 1.685 g of the title compound. $^1$H NMR (CDCl$_3$): 1.02(t,3H), 1.82(m,2H), 2.75 (t,2H), 5.4(brs, 1H), 5.55(brs, 1H), 7.5(s,2H)ppm.

Preparation K 3-n-Propyl-6-methyl-1-(2,4,6-trichlorophenyl)-1H-pyrazolo[3,4-d]pyrimidine-4-ol.

The title compound of Preparation J (1.617 g, 4.85 mmol) and acetamide (3.203 g, 5.42 mmol) were heated at reflux for 5 hours. Liquid chromatography (tlc) indicated that all the starting material was consumed. The mixture was cooled and quenched with water. Precipitate formed and was filtered to give a beige solid. The solid was dissolved in chloroform and water. The organic layer was separated, dried and concentrated to give 1.617 g of brown oil of the title compound. $^1$H NMR (CDCl$_3$): 0.95(t,3H), 1.84(m, 2H), 2.44(s,3H), 2.95(t, 2H), 7.48(s, 2H), 11.15(brs,1H)ppm.

Preparation L

5-Amino-1-napthtyl-3-methylsulfanyl-1H-pyrazole-4-carboxamide.

The title compound was prepared as a yellow solid by the procedure of Preparation A starting with bis(methylsulfanyl)methylenecyanoacetamide and naphthylhydrazine. $^1$H NMR (CDCl$_3$): 2.6(s,3H), 4.0(s,1H), 5.3(brs,1H), 5.45(brs, 1H), 7.45–7.6(m,5H), 7.9–8.05(m,2H)ppm.

Preparation M 3,6-Dimethyl-1(2,4,6-trimethylphenyl)-1H-pyrazolo[3,4-d]pyrimidine-4-ol.

A mixture of 2-cyano-3-ethoxy-but-2-enoic acid amide (573 mg, 3.72 mmol), 2,4,6-trimethylphenylhydrazine HCl salt (695 mg, 3.72 mmol), triethylamine (377 mg, 3.73 mmol) in 5 ml of methanol was heated at reflux for 15 hours. The reaction mixture was cooled and diluted with water, extracted with ethyl acetate. The organic layer was dried and concentrated to give 434 mg of brown solid which was used directly for the next reaction. The brown solid was treated with acetamide (1.600 g, 27 mmol) and heated at reflux for 15 hours. The reaction mixture was cooled, diluted with water and extracted with ethyl acetate. The organic layer was dried and concentrated to give 400 mg of dark-reddish solid which was purified through silica gel column chromatography using chloroform as eluent to give 100 mg of tan solid of the title compound. $^1$H NMR (CDCl$_3$): 2.0(s,3H), 2.3(s, 3H), 2.45(s,3H), 2.65(s,3H), 7.0(s,2H)ppm.

Preparation N

6-Methyl-3-methylsulfanyl-1-(2,4,6-trichlorophenyl)-1H-pyrazolo[3,4-d]pyrimidine-4-ol.

A mixture of 5-amino-1-(2,4,6-trichlorophenyl)-3-methylthiopyrazole-4-carboxamide (7.032 g, 20 mmol) and acetamide (8.850 g, 150 mmol) was heated at reflux for 15 hours. The mixture was cooled and quenched with water and a small amount of methanol. Precipitate formed and was filtered to give 4.343 g (58%) of a brown solid of the title compound. $^1$H NMR (CDCl$_3$): 2.5(s,3H), 2.65(s,3H), 7.5(s, 2H), 12.2(brs,1H)ppm.

Preparation O

6-Methyl-3-methylsulfanyl-1-(2,6-dichloro-4-trifluoromethylphenyl)-1H-pyrazolo[3,4-d]pyrimidine-4-ol.

The title compound was prepared in 66% yield as a yellow solid by the method analogous to that in Preparation N. $^1$N NMR (CDCl$_3$): 2.5(s,3H), 2.65(s,3H), 7.75(s,2H), 11.5(brs, 1H)ppm.

Preparation P

6-Methyl-3-methylsulfanyl-1-(2,4,6-trimethylphenyl)-1H-pyrazolo[3,4-d]pyrimidine-4-ol.

The title compound was prepared in 66% yield as a yellow solid by the method analogous to that in Preparation N. $^1$H NMR (CDCl$_3$): 2.5(s,3H), 2.65(s,3H), 7.75(s,2H), 11.5(brs, 1H)ppm.

Preparation P

6-Methyl-3-methylsulfanyl-1-(2,4,6-trimethylphenyl)-1H-pyrazolo[3,4-d]pyrimidine-4-ol.

A mixture of 5-amino-3-methylsulfanyl-1-(2,4,6-trimethylphenyl)-4-carboxamide (340 mg, 1.17 mmol) and acetamide (691 mg, 11.7 mmol) was heated at reflux for 9 hours. The reaction mixture was quenched with water and extracted with ethyl acetate. The organic layer was dried and concentrated to give the title compound as a brown solid in 74% yield. $^1$H NMR (CDCl$_3$): 2.0(s,6H), 2.3(s,3H), 2.5(s, 3H), 2.6(s,3H), 7.0(s,2H), 11.7(brs,1H)ppm.

Preparation Q

6-Methyl-1-(2,4,6-trichlorophenyl)-1H-pyrazolo[3,4-d]pyrimidine-4-ol was prepared as a tan solid in 91% yield by the method of Preparation P starting with 5-amino-1-(2,4,6-trichlorophenyl)-1H-pyrazole-4-carboxamide. $^1$H NMR (CDCl$_3$): 2.5(s,3H), 7.5(s,2H), 8.3(s,1H)ppm.

3-Methylsulfanyl-1-(2,4,6-trichlorophenyl)-1H-pyrazolo[3,4-d]pyrimidine-4-ol was prepared as a yellow solid in 75% yield by the method of Preparation P starting with 5-amino-3-methylsulfanyl-1-(2,4,6-trichlorophenyl)-1H-pyrazole-4-carboxamide and formamide. $^1$H NMR (CDCl$_3$): 2.65(s,3H), 7.55 and 7.60(2 sets of s,2H), 7.8(s,0.5H), 8.15 and 8.25(2 sets of s,1H) 12.0(brs,0.5H)ppm.

3-Methylsulfanyl-1-(2,6-dichloro-4-trifluoromethylphenyl)-1H-pyrazolo[3,4-d]pyrimidine-4-ol was prepared as a white solid in 83% yield by the method of Preparation P starting with 5-amino-3-methylsulfanyl-1-(2,4-dichloro-6-trifluoromethylphenyl)-1H-pyrazole-4-carboxamide and formamide. $^1$H NMR (CDCl$_3$): 2.6(s,3H), 7.72(s,2H), 8.0(s,1H), 12.1(brs,1H)ppm.

3-Methylsulfanyl-1-(α-naphthyl)-1H-pyrazolo[3,4-d]pyrimidine-4-ol was prepared as a brown solid in 64% yield by the method of Preparation P starting with 5-amino-3-methylsulfanyl-1-(α-naphthyl)-1H-pyrazole-4-carboxamide and formamide. $^1$H NMR (CDCl$_3$): 2.7(s,3H), 7.2–7.7(m, 5H), 7.7–8.1(m,3H)ppm.

3-Methylsulfanyl-6-trifluoromethyl-1-(2,4,6-trichlorophenyl)-1H-pyrazolo[3,4-d]pyrimidine-4-ol was prepared as a white solid, m.p. 220–229° C., in 61% yield by the method of Preparation P starting with 5-amino-3-methylsulfanyl-1-(2,4,6-trichlorophenyl)-1H-pyrazole-4-carboxamide and trifluoroacetamide. $^1$H NMR (CDCl$_3$): 2.6(s,3H), 7.5(s,2H)ppm.

Preparation R

4-Chloro-6-ethyl-3-methylsulfanyl-1-(2,4,6-trichlorophenyl)-1H, pyrazolo[3,4-d]pyrimidine A mixture of 5-amino-3-methylsulfanyl-1-(2,4,6-trichlorophenyl)-1H-pyrazole-4-carboxamide (1.0 g, 2.84 mmol) and propionamide (2.100 g, 28.77 mmol) was heated at 200° C. for 15 hours. The mixture was quenched with water and extracted with ethyl acetate. The organic layer was dried and concentrated to give 600 mg of a crude material which contains the desired product as well as an unidentified compound. The crude material was treated with 1.5 ml of phosphorous oxychloride and heated at reflux for 3 hours. The reaction mixture was cooled and poured over ice-water and stirred. Precipitate formed and was filtered to give 712 mg of the title compound as a brown solid. $^1$H NMR (CDCl$_3$): 1.3(t,3H), 2.7(s,3H), 3.0(q,2H), 7.5(s,2H)ppm.

Preparation S

4-Chloro-3-methylsulfanyl-6-methyl-1-(2,4,6-trichlorophenyl)-1H-pyrazolo[3,4-d]pyrimidine A mixture of 3-methylsulfanyl-6-methyl-1-(2,4,6-trichlorophenyl)-1H-pyrazolo[3,4-d]pyrimidine-4-ol (3.700 g, 9.85 mmol) and phosphorous oxychloride (18.115 g, 11 ml) was heated at reflux for 4 hours. The mixture was cooled and poured over ice-water and stirred for 10 minutes. Precipitate formed and was filtered to give a brown solid. The brown solid was pumped in vacuo to give 3.718 g (96% yield). $^1$H NMR (CDCl$_3$): 2.65(s,3H),2.7(s,3H), 7.5(s,2H) ppm.

Preparation T

The procedure of Preparation S when starting with the appropriate 1H-pyrazolo[3,4-d]pyrimidine-4-ol gave the corresponding 4-chloro-pyrazolo[3,4-d]pyrimidine in Table 5.

TABLE 5

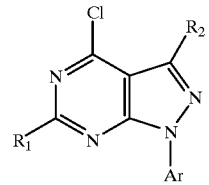

| $R_1$ | $R_2$ | Ar | $^1$H NMR (CDCl$_3$) (ppm) |
|---|---|---|---|
| Me | SMe | 2,6-dichloro-4-trifluoromethylphenyl | 2.65(s,3H), 2.7(s,3H), 7.75(s,2H) |
| Me | SMe | 2,4,6-trimethylphenyl | 1.95(s,6H), 2.35(s,3H), 2.65(s,3H), 2.70(s,3H), 7.0(s,2H) |
| Me | H | 2,4,6-trichlorophenyl | 2.75(s,3H), 7.55(s,2H), 8.35(s,1H) |
| Me | Me | 2,4,6-trichlorophenyl | 2.45(s,3H), 2.65(s,3H), 7.5(s,2H) |
| Me | Me | 2,4,6-trimethylphenyl | 1.90(s,6H), 2.35(s,3H), 2.75(s,3H), 2.80(s,3H), 7.0(s,2H) |
| Me | Et | 2,4,6-trichlorophenyl | 1.42(t,3H), 2.71(s,3H), 3.16(q,2H), 7.51(s,2H) |
| Me | n-Pr | 2,4,6-trichlorophenyl | 1.00(t,3H), 1.87(q,2H), 2.72(s,3H), 3.10(t,2H), 7.50(s,2H) |
| H | SMe | 2,4,6-trichlorophenyl | 2.68(s,3H), 7.78(s,2H), 8.71(s,1H) |
| H | SMe | 2,6-dichloro-4-trifluoromethylphenyl | 2.64(s,3H), 7.72(s,2H), 8.64(s,1H) |
| CF$_3$ | SMe | 2,4,6-trichlorophenyl | 2.68(s,3H), 7.50(s,2H) |

What is claimed is:
1. A compound of the formula

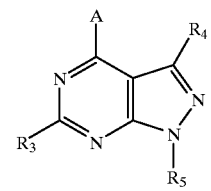

I and the pharmaceutically acceptable acid addition salts thereof, wherein

A is NR$_1$R$_2$, CR$_1$, R$_2$R$_{11}$, or C({CR$_1$R$_{12}$}R$_2$, NHCR$_1$R$_2$R$_{11}$, OCR$_1$R$_2$R$_{11}$, SCR$_1$R$_2$R$_{11}$, NHNR$_1$R$_2$, CR$_2$R$_{11}$NHR$_1$, CR$_2$R$_{11}$OR$_1$, CR$_2$R$_{11}$SR$_1$ or C(O)R$_2$;

R$_1$ is hydrogen, or C$_1$–C$_6$ alkyl which may be substituted by one or two substituents R$_6$ independently selected from the group consisting of hydroxy, fluoro, chloro, bromo, iodo, C$_1$–C$_6$ alkoxy, O—C(O)—(C$_1$–C$_6$ alkyl), O—C(O)—N(C$_1$–C$_4$ alkyl)(C$_1$–C$_2$ alkyl), amino, NH(C$_1$–C$_4$ alkyl), S(C$_1$–C$_6$ alkyl), OC(O)NH(C$_1$–C$_4$ alkyl), N(C$_1$–C$_2$ alkyl)C(O)(C$_1$–C$_4$ alkyl), NHC(O)(C$_1$–C$_4$ alkyl), COOH, CO(C$_1$–C$_4$ alkyl), C(O)NH(C$_1$–C$_4$ alkyl), C(O)N(C$_1$–C$_4$ alkyl)(C$_1$–C$_2$ alkyl), SH, CN, NO$_2$, SO(C$_1$–C$_4$ alkyl), SO$_2$(C$_1$–C$_4$ alkyl), SO$_2$NH(C$_1$–C$_4$ alkyl), SO$_2$N(C$_1$–C$_4$ alkyl)(C$_1$–C$_2$ alkyl), and said C$_1$–C$_6$ alkyl may have one or two double or triple bonds;

R$^2$ is C$_1$–C$_{12}$ alkyl, aryl or (C$_1$–C$_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or (C$_1$–C$_6$ alkylene)cycloalkyl, wherein said cycloalkyl may have one or two of O, S or N—Z, wherein Z is hydrogen, substituted, independently, for one or two carbons of said cycloalkyl, $C_1$–$C_4$ alkyl, benzyl or $C_1$–$C_4$ alkanoyl, wherein $R^2$ may be substituted independently by from one to three of chloro, fluoro, or $C_1$–$C_4$ alkyl, or one of hydroxy, bromo, iodo, $C_1$–$C_6$ alkoxy, OC(O)($C_1$–$C_6$ alkyl), O—C—N($C_1$–$C_4$ alkyl)($C_1$–$C_2$ alkyl), S($C_1$–$C_6$ alkyl), $NH_2$, NH($C_1$–$C_2$ alkyl), N($C_1$–$C_4$ alkyl) C(O)($C_1$–$C_4$ alkyl), NHC(O)($C_1$–$C_4$ alkyl), COOH, C(O)O($C_1$–$C_4$ alkyl), C(O)NH($C_1$–$C_4$ alkyl), C(O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)($C_1$–$C_2$ alkyl), and wherein said $C_1$–$C_{12}$ alkyl or $C_1$–$C_{10}$ alkylene may have one to three double or triple bonds; or $NR_1R_2$ or $CR_1R_2R_{11}$ may form a 4- to 8-membered ring optionally having one or two double bonds or one or two of O, S or N—Z wherein Z is hydrogen, $C_1$–$C_4$ alkyl, benzyl, or $C_1$–$C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl)($C_1$–$C_2$ alkyl), SH, S($C_1$–$C_4$ alkyl), SO($C_1$–$C_4$ alkyl), or $SO_2$($C_1$–$C_4$ alkyl), wherein said $C_1$–$C_4$ alkyl and $C_1$–$C_6$ alkyl may have one or two double or triple bonds and may be substituted by from 1 to 3 substituents $R_7$ independently selected from the group consisting of hydroxy, amino, $C_1$–$C_3$ alkoxy, dimethylamino, diethylamino, methylamino, ethylamino, NHC(O)$CH_3$, fluoro, chloro or $C_1$–$C_3$ thioalkyl;

$R_4$ is hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl) ($C_1$–$C_2$ alkyl), $SO_n$($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(O)($C_1$–$C_4$ alkyl), NH($C_1$–$C_4$ alkyl), N($C_1$–$C_4$ alkyl)($C_1$–$C_2$ alkyl), C(O)O($C_1$–$C_4$ alkyl), $C_1$–$C_3$ alkoxy, $C_1$–$C_3$ thioalkyl, fluoro, bromo, chloro, iodo, cyano or nitro;

$R^5$ is phenyl, naphthyl, thienyl, benzopthienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, or tetrazolyl, wherein each one of the above groups may be substituted independently by from one to three of fluoro, chloro, bromo, formyl, $C_1$–$C_6$ alkyl, $C_1$–$C_6$ alkoxy or trifluoromethyl, or one of hydroxy, iodo, cyano, nitro, amino, cyclopropyl, NH($C_1$–$C_4$ alkyl), N($C_1$–$C_4$ alkyl)($C_1$–$C_2$ alkyl), COO ($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl, $SO_2NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may have one double or triple bond and may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl;

(a) A is not straight chain $C_1$–$C_{12}$ alkyl;
(b) when $R_3$ is hydrogen, A is benzyl or phenethyl, and $R_4$ is fluoro, chloro, bromo or iodo, then $R_5$ is not 5'-deoxy-ribofuranosyl or 5'-amino-5'-deoxy-ribofuranosyl; and
(c) when $R^5$ is phenyl, said phenyl is substituted by two or three substituents.

2. A compound according to claim 1 wherein $R_1$ is $C_1$–$C_4$ alkyl, ($C_2$–$C_4$ alkylene) O($C_1$–$C_4$alkyl), or $C_2$–$C_4$ hydroxyalkyl.

3. A compound according to claim 2 wherein $R_2$ is $C_1$–$C_5$ alkyl.

4. A compound according to claim 2 wherein $R_2$ is ($C_1$–$C_4$ alkylene)aryl wherein said aryl is phenyl, thienyl, benzofuranyl, furanyl, benzothienyl, thiazolyl, pyridyl or benzothiazolyl.

5. A compound according to claim 2 wherein $R_2$ is benzyl, phenylethyl, p-fluorobenzyl, p-chlorobenzyl, p-nitrobenzyl, p-methylbenzyl, p-methoxybenzyl, p-trifluoromethylbenzyl, p-(t-butyl)benzyl, p-ethylbenzyl, (2-thienyl)methyl, (2-thienyl)ethyl, (2-furanyl)methyl, 2-(4-chlorothienyl)methyl, (2-benzofuranyl)methyl, (2-benzothienyl)methyl, (2-thiazolyl)methyl, or (2-benzothiazolyl) methyl.

6. A compound according to claim 5 wherein $R_3$ is methyl, ethyl, methoxy, fluoro or chloro.

7. A compound according to claim 6 wherein $R_4$ is methylthio, methylsulfinyl, methylsulfonyl, hydrogen, methyl, ethyl or n-propyl.

8. A compound according to claim 7 wherein $R_5$ is phenyl substituted by two or three substituents.

9. A compound according to claim 8 wherein said substituent is independently fluoro, chloro, bromo, iodo, $C_1$–$C_4$ alkoxy, trifluoromethyl, $C_1$–$C_5$ alkyl which may be substituted by one of hydroxy, $C_1$–$C_4$ alkoxy or fluoro and may have one double or triple bond, —($C_1$–$C_4$ alkylene)O($C_1$–$C_2$ alkyl), $C_1$–$C_3$ hydroxyalkyl, hydroxy, formyl, COO($C_1$–$C_2$ alkyl), —($C_1$–$C_2$ alkylene)amino, or —C(O)($C_1$–$C_4$ alkyl).

10. A compound according to claim 1 wherein said compound is selected from the group consisting of 3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl}-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)1H-pyrazolo[3,4-d]pyrimidin-4]-yl-amine;

butyl-cyclopropylmethyl-[6-methyl-3-methylsulfanyl-1-(2,4,6-trichlorophenyl)-1H-pyrazolo[3,4-d]pyrimidin-4yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl-amine;

propyl-ethyl-[3,6-dimethyl-1-(2,4,6-trimethylphenyl)-1H-pyrazolo[3,4-d]pyrimidin-4-yl]-amine; and 4-(1-ethyl-propyl)-6-methyl-3-methylsulfanyl-1-(2,4,6-trimethylphenyl)-1H-pyrazolo[3,4-d]pyrimidine.

11. A pharmaceutical composition for the treatment of (a) illnesses induced or facilitated by corticotropin releasing factor or (b) inflammatory disorders which comprises a compound of the formula of claim 1 in an amount effective in the treatment of said illnesses, and a pharmaceutically acceptable carrier.

12. A compound according to claim 2 wherein $R_5$ is phenyl substituted by two or three substituents.

13. A compound according to claim 3 wherein $R_5$ is phenyl substituted by two or three substituents.

14. A compound according to claim 4 wherein $R_5$ is phenyl substituted by two or three substituents.

15. A compound according to claim 5 wherein $R_5$ is phenyl substituted by two or three substituents.

16. A compound according to claim 6 wherein $R_5$ is phenyl substituted by two or three substituents.

17. A compound according to claim 7 wherein $R_5$ is phenyl substituted by two or three substituents.

* * * * *